US011352446B2

(12) United States Patent
Cygnar et al.

(10) Patent No.: US 11,352,446 B2
(45) Date of Patent: *Jun. 7, 2022

(54) METHODS OF MAKING MULTISPECIFIC ANTIGEN-BINDING MOLECULES

(71) Applicant: REGENERON PHARMACEUTICALS, INC., Tarrytown, NY (US)

(72) Inventors: Katherine Cygnar, New York, NY (US); Frank Delfino, Poughquag, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 300 days.

This patent is subject to a terminal disclaimer.

(21) Appl. No.: 16/097,108

(22) PCT Filed: Apr. 28, 2017

(86) PCT No.: PCT/US2017/030250
§ 371 (c)(1),
(2) Date: Oct. 26, 2018

(87) PCT Pub. No.: WO2017/190079
PCT Pub. Date: Nov. 2, 2017

(65) Prior Publication Data
US 2020/0095338 A1 Mar. 26, 2020

Related U.S. Application Data

(60) Provisional application No. 62/328,891, filed on Apr. 28, 2016.

(51) Int. Cl.
*C40B 30/04* (2006.01)
*C07K 16/46* (2006.01)
(Continued)

(52) U.S. Cl.
CPC ........ *C07K 16/468* (2013.01); *C07K 16/1203* (2013.01); *C07K 16/2866* (2013.01);
(Continued)

(58) Field of Classification Search
None
See application file for complete search history.

(56) References Cited

U.S. PATENT DOCUMENTS 4,444,878 A 4/1984 Paulus
4,975,278 A 12/1990 Senter et al.
(Continued)

FOREIGN PATENT DOCUMENTS

JP 2008-506659 3/2008
WO 1998/016254 A1 4/1998
(Continued)

OTHER PUBLICATIONS

Arribas and Cutler, "Weibel-Palade Body Membrane Proteins Exhibit Differential Trafficking After Exocytosis in Endothelial Cells," Traffic, 2000, 1:783-793.
(Continued)

*Primary Examiner* — Christian C Boesen
(74) *Attorney, Agent, or Firm* — FisherBroyles, LLP; Rita S. Wu; Todd R. Samelman

(57) ABSTRACT

The present invention provides multispecific antigen-binding molecules and methods of making or selecting same. The multispecific antigen-binding molecules comprise a first antigen-binding domain that specifically binds a target molecule, and a second antigen-binding domain that specifically binds an internalizing effector protein. The multispecific antigen-binding molecules of the present invention can, in some embodiments, be bispecific antibodies that are capable of binding both a target molecule and an internalizing effector protein. In certain embodiments of the invention, the (Continued)

simultaneous binding of the target molecule and the internalizing effector protein by the multispecific antigen-binding molecule of the present invention results in the attenuation of the activity of the target molecule to a greater extent than the binding of the target molecule alone. In other embodiments of the invention, the target molecule is a tumor associated antigen, and the simultaneous binding of the tumor associated antigen and the internalizing effector protein by the multispecific antigen-binding molecule of the present invention causes or facilitates the targeted killing of tumor cells.

26 Claims, 12 Drawing Sheets

Specification includes a Sequence Listing.

(51) Int. Cl.
    *C07K 16/12*         (2006.01)
    *C07K 16/28*         (2006.01)
    *C07K 16/44*         (2006.01)

(52) U.S. Cl.
    CPC .......... *C07K 16/2896* (2013.01); *C07K 16/44* (2013.01); *C40B 30/04* (2013.01); *C07K 2317/31* (2013.01); *C07K 2317/77* (2013.01)

(56) References Cited

U.S. PATENT DOCUMENTS

| | | | |
|---|---|---|---|
| 5,030,717 | A | 7/1991 | Tramontane et al. |
| 5,126,258 | A | 6/1992 | Lerner et al. |
| 5,156,965 | A | 10/1992 | Schochetman et al. |
| 5,208,020 | A | 5/1993 | Chari et al. |
| 5,229,272 | A | 7/1993 | Paul et al. |
| 5,436,153 | A | 7/1995 | Sprecher et al. |
| 5,500,362 | A | 3/1996 | Robinson et al. |
| 5,585,108 | A | 12/1996 | Ruddy et al. |
| 5,601,819 | A | 2/1997 | Wong et al. |
| 5,602,021 | A | 2/1997 | Davis et al. |
| 5,714,586 | A | 2/1998 | Kunstmann et al. |
| 5,731,168 | A | 3/1998 | Carter et al. |
| 5,821,337 | A | 10/1998 | Carter et al. |
| 5,851,527 | A | 12/1998 | Hansen |
| 5,858,728 | A | 1/1999 | Gram et al. |
| 6,235,714 | B1 | 5/2001 | Paul et al. |
| 6,372,205 | B1 | 4/2002 | Duncan et al. |
| 6,387,674 | B1 | 5/2002 | Trasciatti et al. |
| 6,479,265 | B1 | 11/2002 | Napper et al. |
| 6,703,488 | B1 | 3/2004 | Burton et al. |
| 6,855,804 | B2 | 2/2005 | Paul et al. |
| 7,041,298 | B2 | 5/2006 | Deshaies et al. |
| 7,087,411 | B2 | 8/2006 | Daly et al. |
| 7,105,348 | B2 | 9/2006 | Murphy et al. |
| 7,223,556 | B1 | 5/2007 | Zhou et al. |
| 7,235,641 | B2 | 6/2007 | Kufer et al. |
| 7,335,504 | B2 | 2/2008 | Haupts et al. |
| 7,371,539 | B2 | 5/2008 | Church et al. |
| 7,431,923 | B2 | 10/2008 | Young et al. |
| 7,442,777 | B2 | 10/2008 | Young et al. |
| 7,592,429 | B2 | 9/2009 | Paszty et al. |
| 7,750,116 | B1 | 7/2010 | Doronina et al. |
| 7,754,681 | B2 | 7/2010 | Feng |
| 7,771,997 | B2 | 8/2010 | Chen et al. |
| 7,914,787 | B2 | 3/2011 | Goldenberg et al. |
| 8,058,399 | B2 | 11/2011 | Jung |
| 8,257,745 | B2 | 9/2012 | Ketelson et al. |
| 8,518,403 | B2 | 8/2013 | Hoffmann et al. |
| 8,586,713 | B2 | 11/2013 | Davis et al. |
| 8,815,226 | B2 | 8/2014 | Yurkovetskiy et al. |
| 9,359,437 | B2 | 6/2016 | Davis et al. |
| 9,738,717 | B2 | 8/2017 | Azorsa |
| 9,950,076 | B2 | 4/2018 | Nittoli et al. |
| 2005/0112694 | A1 | 5/2005 | Carter et al. |
| 2006/0099205 | A1 | 5/2006 | Adams et al. |
| 2006/0210474 | A1 | 9/2006 | Young et al. |
| 2007/0041978 | A1 | 2/2007 | Hatiori et al. |
| 2007/0258987 | A1 | 8/2007 | Francisco et al. |
| 2007/0280945 | A1 | 12/2007 | Stevens et al. |
| 2008/0044408 | A1 | 2/2008 | Young et al. |
| 2008/0089891 | A1 | 4/2008 | Hahn et al. |
| 2008/0305497 | A1 | 12/2008 | Kosmeder et al. |
| 2009/0155262 | A1 | 6/2009 | Young et al. |
| 2010/0081796 | A1 | 4/2010 | Brinkmann et al. |
| 2010/0129314 | A1 | 5/2010 | Singh et al. |
| 2010/0233173 | A1 | 9/2010 | Wu et al. |
| 2010/0330034 | A1 | 12/2010 | Bigler et al. |
| 2010/0331527 | A1 | 12/2010 | Davis et al. |
| 2011/0195454 | A1 | 8/2011 | McWhirter et al. |
| 2012/0315276 | A1 | 12/2012 | Otto et al. |
| 2013/0022606 | A1 | 1/2013 | Otto et al. |
| 2013/0101546 | A1 | 4/2013 | Yurkovetskiy et al. |
| 2013/0129739 | A1 | 5/2013 | Otto et al. |
| 2013/0171147 | A1 | 7/2013 | Otto et al. |
| 2013/0243775 | A1 | 9/2013 | Papadopoulos et al. |
| 2013/0272968 | A1 | 10/2013 | Otto et al. |
| 2014/0065158 | A1 | 3/2014 | Ma et al. |
| 2014/0141003 | A1 | 5/2014 | Freiberg et al. |
| 2014/0271659 | A1 | 9/2014 | Ma et al. |
| 2014/0356366 | A1 | 12/2014 | Cheong et al. |
| 2015/0056221 | A1 | 2/2015 | Papadopoulos et al. |
| 2015/0056222 | A1 | 2/2015 | Papadopoulos et al. |
| 2015/0093393 | A1 | 4/2015 | Ma et al. |
| 2015/0252116 | A1 | 9/2015 | Ma et al. |
| 2016/0002342 | A1 | 1/2016 | Ma et al. |
| 2016/0115229 | A1 | 4/2016 | Azorsa |
| 2016/0251442 | A1 | 9/2016 | Papadopoulos et al. |
| 2016/0319029 | A1 | 11/2016 | Freiberg et al. |
| 2016/0375147 | A1 | 12/2016 | Nittoli et al. |
| 2017/0007715 | A1 | 1/2017 | Andreev et al. |
| 2017/0008965 | A1 | 1/2017 | Ma et al. |
| 2017/0209591 | A1 | 7/2017 | Nittoli et al. |
| 2018/0094066 | A1 | 4/2018 | Papadopoulos et al. |
| 2018/0185504 | A1 | 7/2018 | Kelly et al. |

FOREIGN PATENT DOCUMENTS

| | | |
|---|---|---|
| WO | 1999/036437 A1 | 7/1999 |
| WO | 2001/009186 A1 | 2/2001 |
| WO | 2001/036005 A2 | 5/2001 |
| WO | 2005/089808 A2 | 9/2005 |
| WO | 2008/014404 A2 | 1/2008 |
| WO | 2008/019290 A2 | 2/2008 |
| WO | 2008/122039 A2 | 10/2008 |
| WO | 2008/150485 A2 | 12/2008 |
| WO | 2009/094561 A1 | 7/2009 |
| WO | 2009/120922 A2 | 10/2009 |
| WO | 2010/010324 A1 | 1/2010 |
| WO | 2010/115552 A1 | 10/2010 |
| WO | 2010/119119 A1 | 10/2010 |
| WO | 2011/018611 A1 | 2/2011 |
| WO | 2011/029823 A1 | 3/2011 |
| WO | 2011/069794 A1 | 6/2011 |
| WO | 2011/130598 A1 | 10/2011 |
| WO | 2011/147986 A1 | 12/2011 |
| WO | 2012/005982 A2 | 1/2012 |
| WO | 2012/136519 A1 | 10/2012 |
| WO | 2012/143379 A1 | 10/2012 |
| WO | 2012/143523 A1 | 10/2012 |
| WO | 2012/143524 A1 | 10/2012 |
| WO | 2012/166559 A1 | 12/2012 |
| WO | 2013/053872 A1 | 4/2013 |
| WO | 2013/053873 A1 | 4/2013 |
| WO | 2013/055990 A1 | 4/2013 |
| WO | 2013/055993 A1 | 4/2013 |
| WO | 2013/068874 A1 | 5/2013 |
| WO | 2013/085925 A1 | 6/2013 |
| WO | 2013/138400 A1 | 9/2013 |
| WO | 2013/166604 A1 | 11/2013 |
| WO | 2014/065661 A1 | 5/2014 |
| WO | 2014/143909 A1 | 9/2014 |
| WO | 2014/145090 A1 | 9/2014 |

(56) References Cited

FOREIGN PATENT DOCUMENTS

| WO | 2014/182970 A1 | 11/2014 |
|---|---|---|
| WO | 2014/185908 A2 | 11/2014 |
| WO | 2015/026907 A1 | 2/2015 |
| WO | 2015/031396 A1 | 3/2015 |
| WO | 2015/187596 A2 | 12/2015 |
| WO | 2016/160615 A1 | 10/2016 |
| WO | 2017/134197 A1 | 8/2017 |
| WO | 2018/102304 A1 | 6/2018 |
| WO | 2019/011719 A1 | 1/2019 |

OTHER PUBLICATIONS

Bareford and Swann, "Endocytic mechanisms for targeted drug delivery," Advanced Drug Delivery Reviews, Elsevier, Amsterdam, NL, 2007, 59(8):748-758.
Beletskii et al., "High-throughput phagocytosis assay utilizing a pH-sensitive fluorescent dye," BioTechniques, 2005, 39(6):894-897.
Berditchevski et al., "Generation of Monoclonal Antibodies to Integrin-associated Proteins," Journal of Biological Chemistry, Nov. 1997, 272(46):29174-29180.
Bode et al., "Antibody-Directed Fibrinolysis: An Antibody Specific for Both Fibrin and Tissue Plasminogen Activator," Journal of Biological Chemistry, Jan. 1989, 264(2):944-948.
Boersma et al., "DARPins and other repeat protein scaffolds: advances in engineering and applications," Curr. Opin. Biotechnol., 2011, 22:849-885.
Bonardi et al., "Delivery of Saporin to Human B-Cell Lymphoma Using Bispecific Antibody: Targeting via CD22 but not CD19, CD37, or Immunoglobulin Results in Efficient Killing," Cancer Research, Jul. 1993, 53(13):3015-3021.
Dipadova et al., "A Broadly Cross-Protective Monoclonal Antibody Binding to *Escherichia coli* and *Salmonella* Lipopolysaccharides," Infection and Immunity, Sep. 1993, 61(9):3863-3872.
Ghosh et al., "An Endocytosed TGN38 Chimeric Protein is Delivered to the TGN after Trafficking Through the Endocytic Recycling Compartment in CHO Cells," J. Cell Bioi., Aug. 1998, 142(4):923-936.
Gomery et al., "Antibody WN1 222-5 mimics Toll-like receptor 4 binding in the recognition of LPS," Proc. Natl. Acad. Sci USA, 2012, 109(51):20877-20882.
Holliger et al., ""Diabodies": Small bivalent and bispecific antibody fragments," PNAS USA, 1993, 90:6444-6448.
Hua et al., "High-content positional biosensor screening assay for compounds to prevent or disrupt androgen receptor and transcriptional intermediary factor 2 protein-protein interactions," Assay Drug Dev. Technol., 2014,12(7):395-418.
Klein et al., "Progress in overcoming the chain association issue in bispecific heterodimeric IgG antobodies," mAbs, 2012, 4:6 653-663 (12 pages).
Lee et al., "Impaired Retrograde Membrane Traffic Through Endosomes in a Mutant CHO Cell Defective in Phosphalidyl Serine Synthesis," Genes to Cells, 2012, 17:728-736.
Lee et al., "Novel strategy for a bispecific antibody: induction of dual target internalization and degradation," Oncogene, 2016, 35(34):4437-4446.
Li et al., "Dkk1 Stabilizes Wnt Co-Receptor LRP6: Implication for Wnt Ligand-Induced LRP6 Down-Regulation," PLoS One Jun. 2010, 5(6):e11014.
Lieu et al., "The Golgin GCC88 Is Required for Efficient Retrograde Transport of Cargo from the Early Endosomes to the Trans-Golgi Network," Mol. Bioi. Cell, Dec. 2007, 18:4979-4991.
Muller-Loennies, et al., "Identification of a Cross-reactive Epitope Widely Present in Lipopolysaccharide from Enterobacteria and Recognized by the Cross-protective Monoclonal Antibody WN1 222-5," J. Biol. Chem., 2003, 278(28):25618-25627.
Ridgway et al., "'Knobs-into-holes' engineering of antibody CH3 domains for heavy chain heterodimerization," Protein Eng., 1996, 9(7):617-621.

Schiweck et al., "Sequence analysis and bacterial production of the anti-c-myc antibody 9E10: the VH domain has an extended CDR-H3 and exhibits unusual solubility," FEBS Lett., 1997, 414(1):33-38.
Shaner et al., "A guide to choosing fluorescent proteins," Nature Methods, 2011, 2(12):905-909.
Taylor et al., "A transgenic mouse that expresses a diversity of human sequence heavy and light chain immunoglobulins," Nucl. Acids Res., 1992, 20(23):6287-6295.
Yapici et al., "Highly Stable and Sensitive Fluorescent Probes (LysoProbes) for Lysosomal Labeling and Tracking," Scientific Reports, 2015, 5(8576):1-8.
International Search Report and Written Opinion and Received for PCT Application No. PCT/US2017/030250, dated Aug. 4, 2017.
Statement of Relatedness under MPEP 2001.06 with Respect to U.S. Appl. No. 16/097,108 dated Oct. 4, 2019.
Agarwal et al., "A Pictet-Spengler ligation for protein chemical modification," Proc. Natl. Acad. Sci., USA, 2013, 110:46-51.
Ahmad et al., "scFv Antibody: Principles and Clinical Application," Clinical and Developmental Immunology, vol. 2012, article ID 980250, 15 pages.
Al-Lazikani et al., "Standard Conformations for the Canonical Structures of Immunoglobulins," J. Mol. Biol., 1997, 273:927-948.
Altschul et al., "Basic Local Alignment Search Tool," J. Mol. Biol., 1990, 215:403-410.
Altschul et al., "Gapped BLAST and PSI-BLAST: a new generation of protein database search programs," Nucleic Acids Res., 1997, 25(17):3389-3402.
Andreev et al., "Bispecific Antibodies and Antibody-Drug Conjugates (ADCs) Bridging HER2 and Prolactin Receptor Improve Efficacy of HER2 ADCs," Mol. Cancer Ther., Apr. 2017, 16(4):681-693.
Anzai et al., "c-kit associated with the transmembrane 4 superfamily proteins constitutes a functionally distinct subunit in human hematopoietic progenitors," Blood, 2002, 99(12):4413-4421, doi:10.1182/blood.V99.12.4413.
Azad et al., "A fully human CXCR4 antibody demonstrates diagnostic utility and therapeutic efficacy in solid tumor xenografts," Oncotarget, 2016, 7(11):12344-12358.
Beatty et al., "Trafficking from CD63-positive late endocytic multivesicular bodies is essential for intracellular development of Chlamydia trachomatis," Journal of Cell Science, 2006, 119(2):350-359.
Benedict et al., "Determination of the binding affinity of an anti-CD34 single-chain antibody using a novel, flow cytometry based assay," J Immunol Methods., 1997, 201(2):223-231.
Berditchevski et al., "Specific Association of CD63 with the VLA-3 and VLA-6 Integrins," Journal of Biological Chemistry, 1995, 270(30):17784-17790.
Berditchevski et al., "Characterization of Novel Complexes on the Cell Surface between Integrins and Proteins with 4 Transmembrane Domains (TM4 proteins)," Molecular Biology of the Cell, 1996, 7:193-207.
Berditchevski et al., "A Novel Link between Integrins, Transmembrane-4 Superfamily Proteins (CD63 and CD81), and Phosphatidylinositol 4-Kinase*," Journal of Biological Chemistry, Jan. 1997, 272(5):2595-2598.
Berditchevski et al., "Expression of the Palmitoylation-deficient CD151 Weakens the Association of 31 Integrin with the Tetraspanin-enriched Microdomains and Affects Integrin-dependent Signaling*," Journal of Biological Chemistry, 2002, 277(40):36991-37000.
Bostrom et al., "Variants of the Antibody Herceptin That Interact with HER2 and VEGF at the Antigen Binding Site," Science, 2009, 323(5921):1610-1614.
Bouilly et al., "Prolactin signaling mechanisms in ovary," Molecular and Cellular Endocrinology, 2012, 356:80-87.
Carrico et al., "Introducing genetically encoded aldehydes into proteins," Nat. Chem. Biol., 2007, 3:321-322.
Clevenger and Kline, "Prolactin receptor signal transduction," 10(10) Lupus, (2001) 10:706-718.

(56) References Cited

OTHER PUBLICATIONS

Clynes et al., "Fc receptors are required in passive and active immunity to melanoma," Proc. Natl. Acad. Sci. (USA), 1998, 95:652-656.

Core et al., "Hemojuvelin and bone morphogenetic protein (BMP) signaling in iron homeostasis," Frontiers in Pharmacology, May 13, 2014, 5(104):1-9.

De Goeij et al., "Efficient Payload Delivery by a Bispecific Antibody-Drug Conjugate Targeting HER2 and CD63," Mol. Cancer Ther., 2016, 15(11):2688-2697.

Devay et al., "Characterization of proprotein convertase subtilisin/kexin type 9 (PCSK9) trafficking reveals a novel lysosomal targeting mechanism via amyloid precursor-like protein 2 (APLP2)," J. Bioi. Chern., Apr. 2, 2013, 288(15):10805-10818, doi: 10.1074/jbc.M113.453373. Epub Feb. 19, 2013.

Devay et al., "Common Proprotein Convertase Subtilisin/Kexin Type 9 (PCSK9) Epitopes Mediate Multiple Routes for Internalization and Function," PLOS ONE, Apr. 23, 2015, 10(4):e0125127, 20 pages.

Devay et al., "Improved Lysosomal Trafficking Can Modulate the Potency of Antibody Drug Conjugates," Bioconjugate Chem., 2017, 28(4):1102-1114, DOI: 10.1021/acs.bioconjchem.7b00013.

Doronina et al., "Development of potent monoclonal antibody auristatin conjugates for cancer therapy," Nature Biotechnology, 2003, 21(7):778-784 and p. 941 Corrigendum.

Doyle et al., "CD63 is an essential cofactor to leukocyte recruitment by endothelial P-selectin," Blood, 2011, 118(15):4265-427.

Ducry and Stump, "Antibody-Drug Conjugates: Linking Cytotoxic Payloads to Monoclonal Antibodies," Bioconjugate Chem., 2010, 21:5-13.

Duffield et al., "The tetraspanin CD63 enhances the internalization of the H,K-ATPase β-subunit," Proc. Nail. Acad. Sci. USA, Dec. 2003, 100(26):15560-15565.

Egea et al., "Tissue inhibitor of metalloproteinase-1 (TIMP-1) regulates mesenchymal stem cells through let-7f microRNA and Wnt/β-catenin signaling," PNAS, 2012, 109(6):E309-E316.

Ehring, "Hydrogen Exchange/Electrospray Ionization Mass Spectrometry Studies of Structural Features of Proteins and Protein/Protein Interactions," Analytical Biochemistry, 1999, 267(2):252-259.

Eigenbrot et al., "Structural basis for high-affinity HER2 receptor binding by an engineered protein," PNAS, 2010, 107(34):15039-15044.

Engen and Smith, "The Basics of Ion Chromatography," Anal. Chem., 2001, 73:256A-265A.

Engering and Pieters, "Association of distinct tetraspanins with MHC class II molecules at different subcellular locations in human immature dendritic cells," International Immunology, 2001, 13(2):127-134.

Ferland et al., "The effect of chloroquine on lysosomal prolactin receptors in rat liver," Endocrinology, 1984, 115(5):1842-1849.

Flannery et al., "Palmitoylation-dependent association with CD63 targets the CA2+ sensor synaptotagmin VII to lysosomes," J. Cell Biol., Nov. 2010, 191(3):599-613.

Fu et al., "Insights into HER2 signaling from step-by-step optimization of anti-HER2 antibodies," mAbs, 2014, 6(4):978-990.

Genty et al., "Endocytosis and degradation of prolactin and its receptor in Chinese hamster ovary cells stably transfected with prolactin receptor cDNA," Mol. Cell Endocrinol., 1994, 99(2):221-228.

Geuijen et al. "Affinity ranking of antibodies using flow cytometry: Application in antibody phage display-based target discovery," J Immunol Methods, 2005, 302(1-2):68-77.

Gonnet et al., "Exhaustive Matching of the Entire Protein Sequence Database," Science, 1992, 256: 1443-1445.

Gordon et al., "Clinical Activity of Pertuzumab (rhuMAb 2C4), a HER Dimerization Inhibitor, in Advanced Ovarian Cancer: Potential Predictive Relationship With Tumor HER2 Activation Status," mAbs, 2006, 24(26):4324-4332.

Guan et al., "The correlation between the expression of PRL-R and ER/PR in breast cancer," Medline, 2010, 30:596-598, Accession No. 2010210497, 1 page.

Gupta et al., "Dual-targeting immunotherapy of lymphoma: potent cytotoxicity of anti-CD20/CD74 bispecific antibodies in mantle cell or other lymphomas," Blood, Jan. 23, 2012, 119(16):3767-3778.

Hamblett et al., "Effects of Drug Loading on the Antitumor Activity of a Monoclonal Antibody Drug Conjugate," American Association for Cancer Research, Oct. 15, 2004, 10(20):7063-7070.

Hemler et al., (2008) "Targeting of tetraspanin proteins—potential benefits and strategies," Nat. Rev. Drug. Discov. 7(9):747-758, doi:10.1038/nrd2659.

Hevir et al., "Expression of estrogen and progesterone receptors and estrogen metabolizing enzymes in different breast cancer cell lines," Chemico-Biological Interactions, 2011, 191:206-216, doi:10.1016/j.cbi.2010.12.013.

Hirst et al., "Characterization of a Fourth Adaptor-related Protein Complex," Molecular Biology of the Cell, 1999, 10:2787-2802.

Hofer et al., "An engineered selenocysteine defines a unique class of antibody derivatives," Proc. Natl. Acad. Sci., USA, 2008, 105:12451-12456.

Hollander et al., "Selection of Reaction Additives Used in the Preparation of Monomeric Antibody-Calicheamicin Conjugates," Bioconjugate Chem., 2008, 19:358-361.

Horwitz et al., "Variant T47D human breast cancer cells with high progesterone-receptor levels despite estrogen and antiestrogen resistance," Cell. Mar. 1982 28(3):633-642.

Jackson et al., "The nuclear splicing factor RNA binding motif 5 promotes caspase activation in human neuronal cells, and increases after traumatic brain injury in mice," Journal of Cerebral Blood Flow and Metabolism: Official Journal of the International Society of Cerebral Blood Flow and Metabolism, 2015, 35(4):655-666.

Jarantow et al., "Impact of Cell-surface Antigen Expression on Target Engagement and Function of an Epidermal Growth Factor Receptor x c-MET Bispecific Antibody," J Biol Chem.,Oct. 9, 2015, 290(41):24689-24704, doi: 10.1074/jbc.M115.651653.

Jeger et al., "Site-Specific and Stoichiometric Modification of Antibodies by Bacterial Transglutaminase," Angew Chemie, Inter. Ed., 2010, 49:9995-9997.

Junghans et al., "Anti-Tac-H, a Humanized Antibody to the Interleukin 2 Receptor with New Features for Immunotherapy in Malignant and Immune Disorders," Cancer Res. 1990, 50:1495-1502.

Kabat et al., (1991) "Tabulation and Analysis of Amino Acid and Nucleic Acid Sequences of Precursors, V-Regions, C-Regions, J-Chain, T-Cell Receptors for Antigen, T-Cell Surface Antigens, alpha2-Microglobulins, Major Histocompatibility Antigens, Thy-1, Complement, C-Reactive Protein, Thymopoietin, Integrins, Post-gamma Globulin, a 2-Macroglobulins, and Other Related Proteins", Sequences of Proteins of Immunological Interest, Fifth Edition; NIH Publication No. 91-3242, National Institutes of Health, Bethesda, Md. (37 pages).

Kelly et al., "Preclinical Activity of the Novel Anti-Prolactin Receptor (PRLR) Antibody-Drug Conjugate REGN2878-DM1 in PRLR-Positive Breast Cancers," Mol. Cancer Ther., 2017, 16(7):1299-1311, doi:10.1158/1535-7163.MCT-16-0839.Epub Apr. 4, 2017.

Kitani et al., "A Cell Surface Glycoprotein of Rat Basophilic Leukemia Cells Close to the High Affinity IgE Receptor (FcεRI)," Journal of Biological Chemistry, 1991, 266(3):1903-1909.

Kobayashi et al., "The Tetraspanin CD63/lamp3 Cycles between Endocytic and Secretory Compartments in Human Endothelial Cells," Molecular Biology, May 2000, 11:1829-1843.

Kontermann, "Dual targeting strategies with bispecific antibodies," mAbs, 2012, 4(2):182-197.

Kraft et al., "The tetraspanin CD63 is required for efficient IgE-mediated mast cell degranulation and anaphylaxis," J. Immunol, 2013, 191(6):2871-2878.

Kufer et al., "A revival of bispecific antibodies," Trends Biotechnol., 2004, 22(5):238-244.

Lambert and Chari, "Ado-trastuzumab Emtansine (T-DM1): An Antibody-Drug Conjugate (ADC) for HER2-Positive Breast Cancer," Journal of Medicinal Chemistry, (Aug. 28, 2014), 57(16):6949-6964.

(56) References Cited

OTHER PUBLICATIONS

Langer, "New Methods of Drug Delivery," Science, 1990, 249:1527-1533.
Latysheva et al., "Syntenin-1 Is a New Component of Tetraspanin-Enriched Microdomains: Mechanisms and Consequences of the Interaction of Syntenin-1 with CD63," Molecular and Cellular Biology, Oct. 2006, 26(20):7707-7718.
Le Doussal et al., "In Vitro and In Vivo Targeting of Radiolabeled Monovalent and Divalent Haptens with Dual Specificity Monoclonal Antibody Conjugates: Enhanced Divalent Hapten Affinity for Cell-Bound Antibody Conjugate," Journal of Nuclear Medicine, 1989, 30(8):1358.
Lekishvili et al., "The tumour-associated antigen L6 (L6-Ag) is recruited to the tetraspanin-enriched microdomains: implication for tumour cell motility," Journal of Cell Science, 2008, 121(5):685-694, doi:10.1242/jcs.020347.
Levy and Shoham, "The Tetraspanin Web Modulates Immune-Signalling Complexes," Nat. Rev. Immunol., 2005, 5(2):136-148.
Li et al., "Cell Type and Culture Condition-Dependent Alternative Splicing in Human Breast Cancer Cells Revealed by Splicing-Sensitive Microarrays," Cancer Res., Feb. 15, 2006, 66(4):1990-1999.
Lloyd et al., "Modelling the human immune response: performance of a $10^{11}$ human antibody repertoire against a broad panel of therapeutically relevant antigens," Protein Engineering, Design & Selection, 2009, 22(3):159-168.
Mabry et al., "A dual-targeting PDGFRβ/VEGF-A molecule assembled from stable antibody fragments demonstrates anti-angiogenic activity invitro and in vivo," mAbs, 2010, 2(1):20-34.
Maecker et al., "The tetraspanin superfamily: molecular facilitators," FASEB J., May 1997, 11(6)428-442.
Mantegazza et al., "CD63 Tetraspanin Slows Down Cell Migration and Translocates to the Endosomal-Lysosomal-MIICs Route after Extracellular Stimuli in Human Immature Dendritic Cells," Blood, Aug. 2004, 104(4):1183-1190.
Martin et al., "Modeling antibody hypervariable loops: A combined algorithm," Proc. Natl. Acad. Sci. USA, 1989, 86:9268-9272.
Martin et al., "Tetraspanins in Viral Infections: a Fundamental Role in Viral Biology?," Journal of Virology, 2005, 79(17):10839-10851.
Matsuda et al. "BRI3 inhibits amyloid precursor protein processing in a mechanistically distinct manner from its homologue dementia gene BRI2," Journal of Biological Chemistry, 2009, 284(23):15816.
McDonagh et al., "Antitumor Activity of a Novel Bispecific Antibody That Targets the ErbB2/ErbB3 Oncogenic Unit and Inhibits Heregulin-Induced Activation of ErbB3", Molecular Cancer Therapeutics, Mar. 2012, 11(3):582-593, XP002684950, ISSN: 1535-7163, DOI:10.1158/1535-7163.MCT-11-0820.
Metzelaar et al., "CD63 antigen. A novel lysosomal membrane glycoprotein, cloned by a screening procedure for intracellular antigens in eukaryotic cells," J. Biol. Chem., 1991, 266(5):3239-3245.
Mordenti et al., "Interspecies Scaling of Clearance and Volume of Distribution Data for Five Therapeutic Proteins," Pharmaceutical Research, 1991, 8:1351-1359.
Nishibori et al., "The Protein CD63 Is in Platelet Dense Granules, Is Deficient in a Patient with Hermansky-Pudlak Syndrome, and Appears Identical to Granulophysin," J. Clin. Invest., 1993, 91(4):1775-1782.
Ollivier-Bousquet "Transferrin and Prolactin Transcytosis in the Lactating Mammary Epithelial Cell," Journal of Mammary Gland Biology and Neoplasia, 1998, 3(3):303-313.
Otto, et al., "A Neutralizing Prolactin Receptor Antibody Whose In Vivo Application Mimics the Phenotype of Female Prolactin Receptor-Deficient Mice," Endocrinology, 2015, 156: 4365-4373.
Pandey et al., "Amyloid precursor-like protein 2 (APLP2) affects the actin cytoskeleton and increases pancreatic cancer growth and metastasis," Oncotarget. Feb. 10, 2015, 6(4):2064-2075.
Pandey et al., "Amyloid precursor protein and amyloid precursor-like protein 2 in cancer," Oncotarget. Apr. 12, 2016, 7(15):19430-19444, doi:10.18632/oncotarget.7103.
Paschkowsky et al., "Alternative Processing of the Amyloid Precursor Protein Family by Rhomboid Protease RHBDL4," Journal of Biological Chemistry, 2016, 291(42): 21903-21912.
Pearson, "Using the FASTA Program to Search Protein and DNA Sequence Databases," Chapter 26, Methods Mol. Biol., 1994, 26:307-331.
Poljak et al., "Production and structure of diabodies," Structure, 1994, 2:1121-1123.
Pols and Klumperman, "Trafficking and Function of the Tetraspanin CD63," Exp. Cell Res., Oct. 2009, 315:1584-1592.
Powell et al., "Compendium of Excipients for Parenteral Formulations" PDA J. Pharm. Sci. Technol., 1998, 52:238-311.
Rabuka et al., "Site-specific chemical protein conjugation using genetically encoded aldehyde tags," Nat. Protocols, 2012, 7(6):1052-1067.
Reineke, "Antibody Epitope Mapping Using Arrays of Synthetic Peptides," Methods Mol. Biol., Chapter 26, 2004, 248:443-463.
Rhoden et al., "A Modeling and Experimental Investigation of the Effects of Antigen Density, Binding Affinity, and Antigen Expression Ratio on Bispecific Antibody Binding to Cell Surface Targets," J Biol. Chem. 291, May 2016, 291(21):11337-11347, doi: 10.1074/jbc.M116.714287.
Robinson et al., "Targeting ErbB2 and ErbB3 with a bispecific single-chain Fv enhances targeting selectivity and induces a therapeutic effect in vitro", British Journal of Cancer, vol. 99, No. 9, Oct. 28, 2008 (Oct. 28, 2008), pp. 1415-1425, XP009115294, ISSN: 0007-0920, DOI: 10.1038/SJ.BJC. 6604700.
Rous et al., "Role of Adaptor Complex AP-3 in Targeting Wild-Type and Mutated CD63 to Lysosomes," Molecular Biology of the Cell, Mar. 2002, 13:1071-1082.
Rubinstein et al., "CD9, CD63, CD81, and CD82 are components of a surface tetraspan network connected to HLA-DR and VLA integrins," Eur. J. Immunol., 1996, 26:2657-2665.
Ryan et al., "Polyclonal Antibody Production Against Chito-Oligosaccharides," Food & Agriculture Immunol., 2001, 13:127-130.
Sapra et al., "Monoclonal antibody-based therapies in cancer: Advances and challenges," Pharmacol. & Therapeutics, 2013, 138:452-469.
Schröder et al., "Deficiency of the Tetraspanin CD63 Associated with Kidney Pathology but Normal Lysosomal Function," Mol. Cell. Biol., 2009, 29(4):1083-1094.
Schumacher et al., "Current Status: Site-Specific Antibody Drug Conjugates," J. Clin. Immunol., 2016, 36(Suppl 1):S100-S107.
Scotti et al., "Additive effects of a prolactin receptor antagonist, G129R, and herceptin on inhibition of HER2-overexpressing breast cancer cells," Breast Cancer Research and Treatment, 2008, 111:241-250.
Sefton, "Implantable Pumps," CRC Crit. Ref. Biomed. Eng., 1987, 14(3):201-240.
Senter, "Activation of Prodrugs by Antibody-Enzyme Conjugates: A New Approach to Cancer Therapy," FASEB J., 1990, 4:188-193.
Shahied et al., "Bispecific Minibodies Targeting HER2/neu and CD16 Exhibit Improved Tumor Lysis When Placed in a Divalent Tumor Antigen Binding Format," J. Bioi. Chern., Dec. 2004, 279(52):53907-53914.
Sharkey et al., "Bispecific Antiibody Pretargeting of Radionuclides for Immuno-Single-Photon Emission Computed Tomography and Immuno-Positron Emission Tomography Molecular Imaging: An Update," Clinical Cancer Research, 2007, 13(18 Suppl):5577s-5585s.
Shaunak et al., "Site-specific PEGylation of native disulfide bonds in therapeutic proteins," Nat. Chem. Biol., 2006, 2(6):312-313.
Shen et al., "A map of the cis-regulatory sequences in the mouse genome," Nature, 2012, 488(7409):116-120, doi:10.1038/nature11243.
Shields et al., "Lack of Fucose on Human IgG1 N-Linked Oligosaccharide Improves Binding to Human Fc RIII and Antibody-dependent Cellular Toxicity," Journal of Biological Chemistry, 2002, 277(30):26733-26740.
Shimamoto et al., "Peptibodies: A flexible alternative format to antibodies," Mabs, 2012, 4(5):586-591.

(56) References Cited

OTHER PUBLICATIONS

Skubitz et al., "CD63 associates with tyrosine kinase activity and CD11/CD18, and transmits an activation signal in neutrophils," Journal of Immunology, 1996, 157:3617-3626.

Takino et al., "Tetraspanin CD63 promotes targeting and lysosomal proteolysis of membrane-type 1 matrix metalloproteinase," Biochem. Biophys. Res. Commun., 2003, 304:160-166.

Tam et al., "A bispecific antibody against human IgE and human FcγRII that inhibits antigen-induced histamine release by human mast cells and basophils," Allergy, 2004, 59:772-780.

Tavare et al., "An effective immuno-PET imaging method to monitor CD8-dependent responses to immunotherapy," Cancer Res., 2016, 76(1):73-82.

Tomer, "Characterization of a discontinuous epitope of the human immunodeficiency virus (HIV) core protein p24 by epitope excision and differential chemical modification followed by mass spectrometric peptide mapping analysis," Protein Science, 2000, 9:487-496.

Tuli et al., "Mechanism for amyloid precursor-like protein 2 enhancement of major histocompatibility complex class I molecule degradation," J Biol Chem. 2009, 284(49):34296-34307, doi: 10.1074/jbc.M109.039727. Epub Oct. 6, 2009.

Tuscano et al., "The Bs20x22 anti-CD20-CD22 bispecific antibody has more lymphomacidal activity than do the parent antibodies alone," Cancer Immunol. Immunother., Feb. 24, 2011, 60(6):771-780.

Tutt et al., "Trispecific F(ab')$_3$ Derivatives That Use Cooperative Signaling Via the TCR/CD3 Complex and CD2 To Activate and Redirect Resting Cytotoxic T Cells," J. Immunol., 1991, 147(1):60-69.

Van't Veer and Van Der Poll, "Keeping blood clots at bay in sepsis," Nature Medicine, Jun. 2008, 14(6):606-608.

Vincent and Zurini, "Current strategies in antibody engineering: Fc engineering and pH-dependent antigen binding, bispecific antibodies and antibody drug conjugates," Biotechnol. J., 2012, 7:1444-1450.

Ward et al., "Binding activities of a repertoire of single immunoglobulin variable domains secreted from *Escherichia coli*," Nature, 1989, 341:544-546.

Wu et al., "Receptor-mediated in Vitro Gene Transformation by Soluble DNA Carrier System," J. Biol. Chem., 1987, 262(10):4429-4432.

Yauch and Hemler, "Specific interactions among transmembrane 4 superfamily (TM4SF) proteins and phosphoinositide 4-kinase," Biochem. J., 2000, 351:629-637.

Yoshida et al., "A CD63 Mutant Inhibits T-cell Tropic Human Immunodeficiency Virus Type 1 Entry by Disrupting CXCR4 Trafficking to the Plasma Membrane," Traffic, Feb. 2008, 9:540-558.

R&D Systems: "Monoclonal—Anti-human APLP-2 Antibody—Catalog No. MAB4945," R&D Systems Online Catalogue, 2019, https://resources.rndsystems.com/pdfs/datasheets/mab4945.pdf.

Atlas Antibodies: "Anti-APLP2 Product Datasheet—Product No. HPA039319," Atlas Antibodies Online Catalogue, 2019, https://atlasantibodies.com/api/print_datasheet/HPA039319.pdf.

International Search Report and Written Opinion for PCT/US2016/065647, dated Jun. 8, 2017.

International Search Report and Written Opinion Received for PCT Application No. PCT/US2013/030636, dated Aug. 6, 2013.

International Search Report and Written Opinion and Received for PCT Application No. PCT/US2016/041055, dated Dec. 5, 2016.

Brissinck et al. (1993) "Bispecific Antibodies in Lymphoma" Intern. Rev. Immunol., 10(2-3):187-94.

Caplus Accession No. 1990:211724 (1990).

Schanzer et al. (Jul. 2014) "A Novel Glycoengineered Bispecific Antibody Format for Targeted Inhibition of Epidermal Growth Factor Receptor (EGFR) and Insulin-like Growth Factor Receptor Type I (IGF-1R) Demonstrating Unique Molecular Properties" J. Biol. Chem., 289(27):18693-706.

Life Technologies/ThermoFisher scientific product 35-9200 https://www.thermofisher.com/antibody/product/Prolactin-Receptor-Antibody-clone-1A2B1-Monoclonal/35-9200 (Accessed on Mar. 19, 2019).

Trastuzumab https://www.accessdata.fda.gov/drugsatfda_docs/label/1998/trasgen092598lb.pdf (Sep. 1998).

Dako A0485 https://www.agilent.com/cs/library/packageinsert/public/103814005.PDF (2013).

Abcam: "Anti-APLP2 antibody ab128603" abcam Online Catalogue (Aug. 29, 2019), retrieved from internet, https://www.abcam.com/aplp2-antibody-ab128603.pdf.

[Note: non-NPL document; included here for convenience, but also communicated separately] Statement of Relatedness under MPEP 2001.06 with Respect to U.S. Appl. No. 16/097,108, dated Jul. 1, 2021.

SEQUENCE LISTING

```
<160> NUMBER OF SEQ ID NOS: 4

<210> SEQ ID NO 1
<211> LENGTH: 502
<212> TYPE: PRT
<213> ORGANISM: Artificial sequence
<220> FEATURE:
<223> OTHER INFORMATION: synthetic

<400> SEQUENCE: 1
```

-continued

```
Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
        50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
                100                 105                 110

Ala Cys Arg Lys Arg Lys Arg Cys Met Arg His Ala Met Cys Cys
        115                 120                 125

Pro Gly Asn Tyr Cys Lys Asn Gly Ile Cys Val Ser Ser Asp Gln Asn
        130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
                180                 185                 190

Ser Asp Cys Ala Ser Gly Leu Cys Cys Ala Arg His Phe Trp Ser Lys
        195                 200                 205

Ile Cys Lys Pro Val Leu Lys Glu Gly Gln Val Cys Thr Lys His Arg
210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His Gly Pro Gly Glu Pro Arg
        260                 265                 270

Gly Pro Thr Ile Lys Pro Cys Pro Pro Cys Lys Cys Pro Ala Pro Asn
        275                 280                 285

Leu Leu Gly Gly Pro Ser Val Phe Ile Phe Pro Pro Lys Ile Lys Asp
        290                 295                 300

Val Leu Met Ile Ser Leu Ser Pro Ile Val Thr Cys Val Val Val Asp
305                 310                 315                 320

Val Ser Glu Asp Asp Pro Asp Val Gln Ile Ser Trp Phe Val Asn Asn
                325                 330                 335

Val Glu Val His Thr Ala Gln Thr Gln Thr His Arg Glu Asp Tyr Asn
                340                 345                 350

Ser Thr Leu Arg Val Val Ser Ala Leu Pro Ile Gln His Gln Asp Trp
        355                 360                 365

Met Ser Gly Lys Glu Phe Lys Cys Lys Val Asn Asn Lys Asp Leu Pro
        370                 375                 380

Ala Pro Ile Glu Arg Thr Ile Ser Lys Pro Lys Gly Ser Val Arg Ala
385                 390                 395                 400

Pro Gln Val Tyr Val Leu Pro Pro Pro Glu Glu Glu Met Thr Lys Lys
                405                 410                 415
```

```
Gln Val Thr Leu Thr Cys Met Val Thr Asp Phe Met Pro Glu Asp Ile
            420                 425                 430

Tyr Val Glu Trp Thr Asn Asn Gly Lys Thr Glu Leu Asn Tyr Lys Asn
435                 440                 445

Thr Glu Pro Val Leu Asp Ser Asp Gly Ser Tyr Phe Met Tyr Ser Lys
            450                 455                 460

Leu Arg Val Glu Lys Lys Asn Trp Val Glu Arg Asn Ser Tyr Ser Cys
465                 470                 475                 480

Ser Val Val His Glu Gly Leu His Asn His Thr Thr Lys Ser Phe
            485                 490                 495

Ser Arg Thr Pro Gly Lys
            500

<210> SEQ ID NO 2
<211> LENGTH: 496
<212> TYPE: PRT
<213> ORGANISM: Artificial sequence
<220> FEATURE:
<223> OTHER INFORMATION: synthetic

<400> SEQUENCE: 2

Met Met Ala Leu Gly Ala Ala Gly Ala Thr Arg Val Phe Val Ala Met
1               5                   10                  15

Val Ala Ala Leu Gly Gly His Pro Leu Leu Gly Val Ser Ala Thr
            20                  25                  30

Leu Asn Ser Val Leu Asn Ser Asn Ala Ile Lys Asn Leu Pro Pro Pro
            35                  40                  45

Leu Gly Gly Ala Ala Gly His Pro Gly Ser Ala Val Ser Ala Ala Pro
        50                  55                  60

Gly Ile Leu Tyr Pro Gly Gly Asn Lys Tyr Gln Thr Ile Asp Asn Tyr
65                  70                  75                  80

Gln Pro Tyr Pro Cys Ala Glu Asp Glu Glu Cys Gly Thr Asp Glu Tyr
                85                  90                  95

Cys Ala Ser Pro Thr Arg Gly Gly Asp Ala Gly Val Gln Ile Cys Leu
            100                 105                 110

Ala Cys Arg Lys Arg Arg Lys Arg Cys Met Arg His Ala Met Cys Cys
            115                 120                 125

Pro Gly Asn Tyr Cys Lys Asn Gly Ile Cys Val Ser Ser Asp Gln Asn
        130                 135                 140

His Phe Arg Gly Glu Ile Glu Glu Thr Ile Thr Glu Ser Phe Gly Asn
145                 150                 155                 160

Asp His Ser Thr Leu Asp Gly Tyr Ser Arg Arg Thr Thr Leu Ser Ser
                165                 170                 175

Lys Met Tyr His Thr Lys Gly Gln Glu Gly Ser Val Cys Leu Arg Ser
            180                 185                 190

Ser Asp Cys Ala Ser Gly Leu Cys Cys Ala Arg His Phe Trp Ser Lys
            195                 200                 205

Ile Cys Lys Pro Val Leu Lys Glu Gly Gln Val Cys Thr Lys His Arg
        210                 215                 220

Arg Lys Gly Ser His Gly Leu Glu Ile Phe Gln Arg Cys Tyr Cys Gly
225                 230                 235                 240

Glu Gly Leu Ser Cys Arg Ile Gln Lys Asp His His Gln Ala Ser Asn
                245                 250                 255

Ser Ser Arg Leu His Thr Cys Gln Arg His Gly Pro Gly Asp Lys Thr
            260                 265                 270
```

```
His Thr Cys Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

<210> SEQ ID NO 3
<211> LENGTH: 122
<212> TYPE: PRT
<213> ORGANISM: Artificial sequence
<220> FEATURE:
<223> OTHER INFORMATION: synthetic

<400> SEQUENCE: 3

Glu Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Asp Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Ile Lys Tyr Phe Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala His Tyr Tyr Cys
                85                  90                  95

Ala Lys Glu Ser Ser Ser Trp Tyr Phe Tyr His Gly Leu Asp Val Trp
                100                 105                 110

Gly Gln Gly Thr Met Val Thr Val Ser Ser
            115                 120

<210> SEQ ID NO 4
<211> LENGTH: 114
```

```
<212> TYPE: PRT
<213> ORGANISM: Artificial sequence
<220> FEATURE:
<223> OTHER INFORMATION: synthetic

<400> SEQUENCE: 4

Glu Ile Val Met Thr Gln Ser Pro Leu Ser Leu Pro Val Ser Pro Gly
1               5                   10                  15

Glu Pro Ala Ser Ile Ser Cys Arg Ser Asn Gln Ser Leu Leu His Ser
            20                  25                  30

Asn Gly Asn Asn Tyr Leu Ala Trp Tyr Leu Gln Lys Pro Gly Gln Ser
        35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Gly Asp Val Gly Thr Tyr Phe Cys Met Gln Ser
                85                  90                  95

Leu Gln Ala Pro Pro Phe Thr Phe Gly Pro Gly Thr Lys Val Glu Ile
            100                 105                 110

Lys Arg
```

METHODS OF MAKING MULTISPECIFIC ANTIGEN-BINDING MOLECULES

This application is a U.S. National Phase Application filed under 35 U.S.C. § 371 of PCT Application No. PCT/US2017/030250, filed Apr. 28, 2017, which claims priority to U.S. Provisional Application Ser. No. 62/328,891, filed Apr. 28, 2016, each of which applications is hereby incorporated by reference in its entirety.

FIELD OF THE INVENTION

The present invention relates to the field of therapeutic proteins, and in particular, to the field of therapeutic proteins that are capable of inactivating, blocking, attenuating, eliminating and/or reducing the concentration of one or more target molecules in vitro or in vivo.

BACKGROUND

Therapeutic treatments often require the inactivation or blocking of one or more target molecules that act on or in the vicinity of a cell. For example, antibody-based therapeutics often function by binding to a particular antigen expressed on the surface of a cell, or to a soluble ligand, thereby interfering with the antigen's normal biological activity. Antibodies and other binding constructs directed against various cytokines (e.g., IL-1, IL-4, IL-6, IL-13, IL-22, IL-25, IL-33, etc.), or their respective receptors, for instance, have been shown to be useful in treating a wide array of human ailments and diseases. Therapeutic agents of this type typically function by blocking the interaction between the cytokine and its receptor in order to attenuate or inhibit cellular signaling. In certain contexts, however, it would be therapeutically beneficial to inactivate or inhibit the activity of a target molecule in a manner that does not necessarily involve blocking its physical interaction with another component. One way in which such non-blocking attenuation of a target molecule could be achieved would be to reduce the extracellular or cell surface concentration of the target molecule. Although genetic and nucleic acid-based strategies for reducing the amount or concentration of a given target molecule are known in the art, such strategies are often fraught with substantial technical complications and unintended side effects in therapeutic settings. Accordingly, alternative non-blocking strategies are needed to facilitate the inactivation or attenuation of various target molecules for therapeutic purposes.

BRIEF SUMMARY OF THE INVENTION

The present invention is based, at least in part, on the concept of attenuating or inactivating a target molecule by linking the target molecule and a destroyer protein or other internalizing effector protein. The target molecule is internalized into the cell along with the internalizing effector protein, and processed by the intracellular degradative machinery, or otherwise attenuated, sequestered, or inactivated.

Accordingly, in one aspect, the invention provides a multispecific antigen-binding molecule that is capable of binding a target molecule (T) and an internalizing effector protein (E). A subset of internalizing effectors includes those proteins that lead to the destruction of the target (a.k.a. destroyers, destroyer proteins, or $E_D$), such as by degradation in the lysosome. More specifically, the invention provides a multispecific antigen-binding molecule comprising a first antigen-binding domain (D1), and a second antigen-binding domain (D2), wherein D1 specifically binds T, and D2 specifically binds E, and wherein the binding of both T and E by the multispecific antigen-binding molecule attenuates the activity of T to a greater extent than the binding of T by D1 alone. In some embodiments of any aspect, the target is a therapeutically relevant target, such as IL-1, IL-1 receptor, IL-4, IL-4 receptor, VEGF, VEGF receptor, RSV, NGF, NGF receptor, programmed cell death protein-1 (PD1), programmed cell death protein ligand-1 (PD-L1), PD-L2, PDGF, PDGF receptor, angiopoietin-2 (Ang2), Ang2 receptor, myostatin (GDF8), GDF8 receptor, CD3, CD20, and the like. In one embodiment, the multispecific antigen-binding molecule is a bispecific antibody, wherein one arm contains the first antigen-binding domain (D1), and the other arm contains the second antigen-binding domain (D2).

In another aspect, the invention provides methods of making or selecting a multispecific antigen-binding molecule capable of inactivating or attenuating the activity of a target molecule (T). In one embodiment, the method comprises the steps of (1) combining a first antigen-binding domain (that binds target) with a second antigen-binding domain (that binds destroyer), (2) contacting the combination and a labeled target molecule to a cell that expresses a destroyer protein, (3) incubating the cell for a time sufficient to allow internalization of the labeled target, (4) detecting the internalized label, and (5) selecting the combination of first and second binding domains. In one embodiment, the first antigen-binding domain (a.k.a. target-binding domain) does not block target activity alone or as a bivalent monospecific target-binding protein. In some embodiments, either one or the other of the first and second binding domain may be selected and combined with another binding domain that is known or discovered to be effective as part of a multispecific antigen-binding protein.

In some embodiments, the destroyer protein is known or discovered to traffic to or from the lysosome. In some embodiments, the destroyer protein is known or discovered to be rapidly turned-over. In some embodiments, the destroyer molecule is known or discovered to rapidly clear a destroyer-specific bivalent monospecific antibody. Non-limiting examples of destroyer molecules include PCSK9, MHC-1, APLP2, LDLR, CD63, mannose-6-phosphate receptor (MPR), LIMP-2, sortilin, and the like.

In some embodiments, the destroyer molecule, when aggregated on the cell surface upon contact with inter alia (i) a multispecific antigen binding protein engaged with its cognate target (T), or (ii) a monospecific bivalent antigen binding protein (e.g., monospecific monoclonal antibody), is rapidly turned over or is rapidly cleared from the cell surface. In some embodiments, rapidly cleared or rapidly turned over includes clearance from the cell surface at a $t_{1/2}$ of <65 hours, <60 hours, <55 hours, <50 hours, <45 hours, <40 hours, <35 hours, <34 hours, <33 hours, <32 hours, <31 hours, <30 hours, <29 hours, <28 hours, <27 hours, <26 hours, <25 hours, <24 hours, <23 hours, <22 hours, <21 hours, <20 hours, <19 hours, <18 hours, <17 hours, <16 hours, <15 hours, <14 hours, <13 hours, <12 hours, <11 hours, <10 hours, <9 hours, <8 hours, <7 hours, <6 hours, <5 hours, <4 hours, <3 hours, <2 hours, <1 hours, or <30 minutes.

In some embodiments, an effective internalizing destroyer-binding arm is selected by (1) combining one of several potential destroyer binding domains with a known effective target-binding domain, (2) contacting the combination and a labeled target molecule to a cell that expresses a destroyer protein, (3) incubating the cell for a time sufficient to allow internalization of the labeled target, (4) detecting the internalized label, (5) selecting the combination of binding domains, and (6) selecting the effective destroyer-binding domain. In one embodiment, the known effective target contains a myc epitope and the known effective target-binding domain binds the myc epitope. In other embodiments, either one or the other of the first and second binding domain may be selected and combined with another binding domain known to be effective.

In some embodiments of any aspect, the multispecific antigen-binding protein is a bispecific antibody. Here, the target-specific arm of the bispecific antibody comprises an immunoglobulin heavy chain and comprises the target-specific binding domain; and the destroyer-specific arm of the bispecific antibody comprises an immunoglobulin heavy chain and comprises the destroyer-specific binding domain. In some embodiments, the bispecific antibody comprises a single (common) light chain. In some embodiments, one of the heavy chains (either the target-specific or the destroyer-specific, but not both) contains a mutation that affects protein A binding, such as an H95R modification (by IMGT exon numbering; H435R by EU numbering).

Other embodiments will become apparent from a review of the ensuing detailed description.

DRAWINGS

FIG. 1 (panels A-D) provides schematic representations of four general exemplary mechanisms of action for the multispecific antigen binding molecules of the present invention. In each illustrated configuration D1 is a first antigen-binding domain; D2 is a second antigen binding domain; T is a target molecule; E is an internalizing effector protein; and R is a receptor which internalizes upon binding E. Panel A depicts the situation in which both T and E are membrane-associated. Panel B depicts the situation in which T is soluble and E is membrane-associated. Panel C depicts the situation in which T is membrane-associated and E is a soluble protein that interacts with, and is internalized into the cell via the interaction of E and R. Panel D depicts the situation in which T is soluble and E is a soluble protein that interacts with, and is internalized into the cell via the interaction of E and R.

Figure 3:
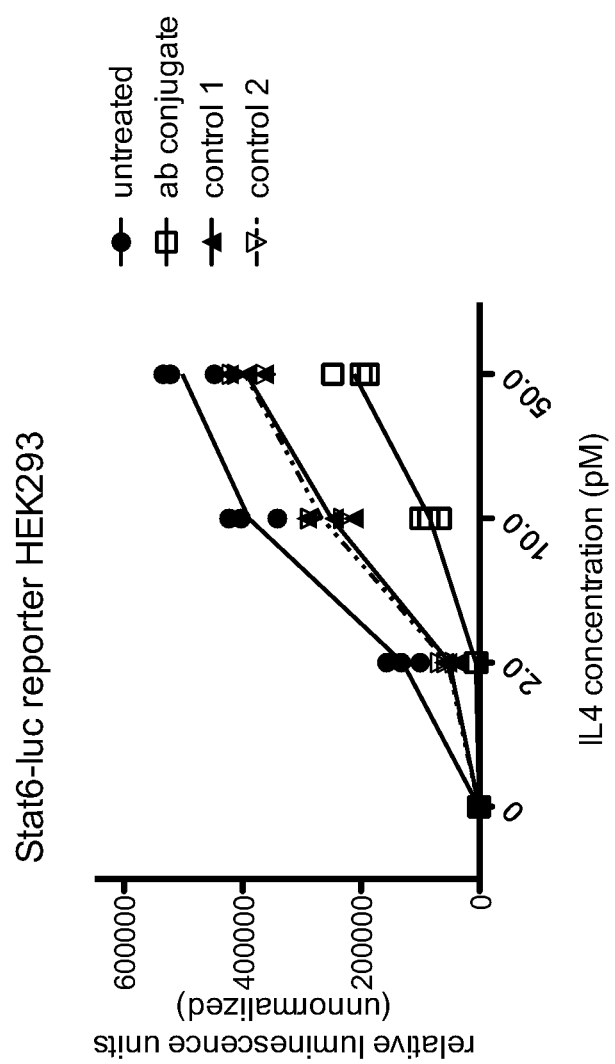
FIG. 3 shows the relative IL-4-induced luminescence produced by Stat6-luc reporter HEK293 cells in the presence and absence of an anti-IL-4R/anti-CD63 multispecific antigen binding protein ("ab conjugate") or control constructs ("control 1" and "control 2") at various concentrations of IL-4.
Figure 4:
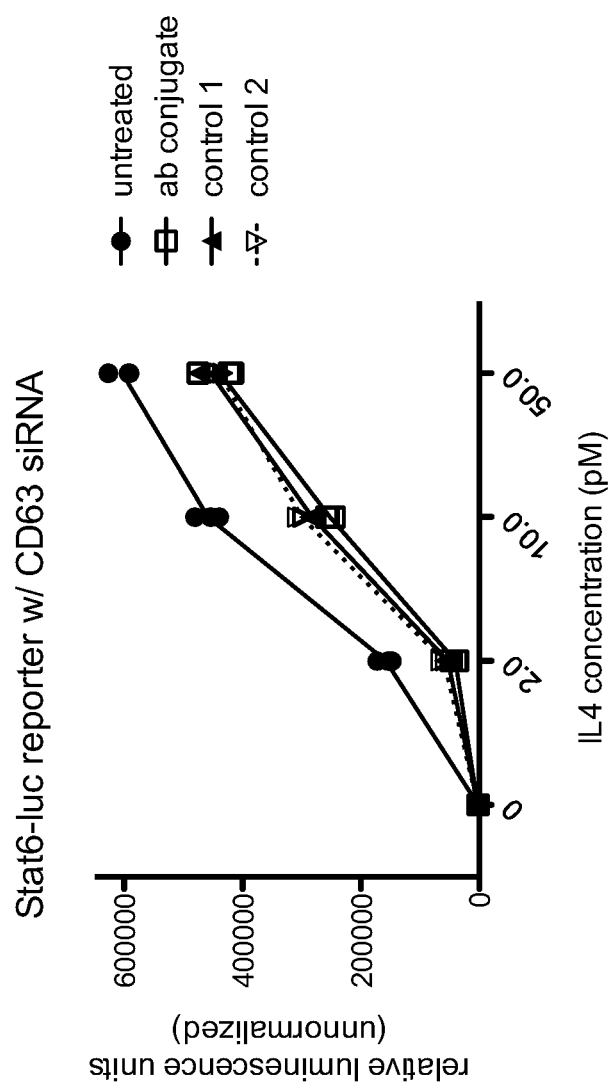
FIG. 4 shows the results of an experiment carried out in the same manner as the experiment shown in FIG. 3, except that CD63 expression was significantly reduced in the reporter cell line by an siRNA directed against CD63.
Figure 5:
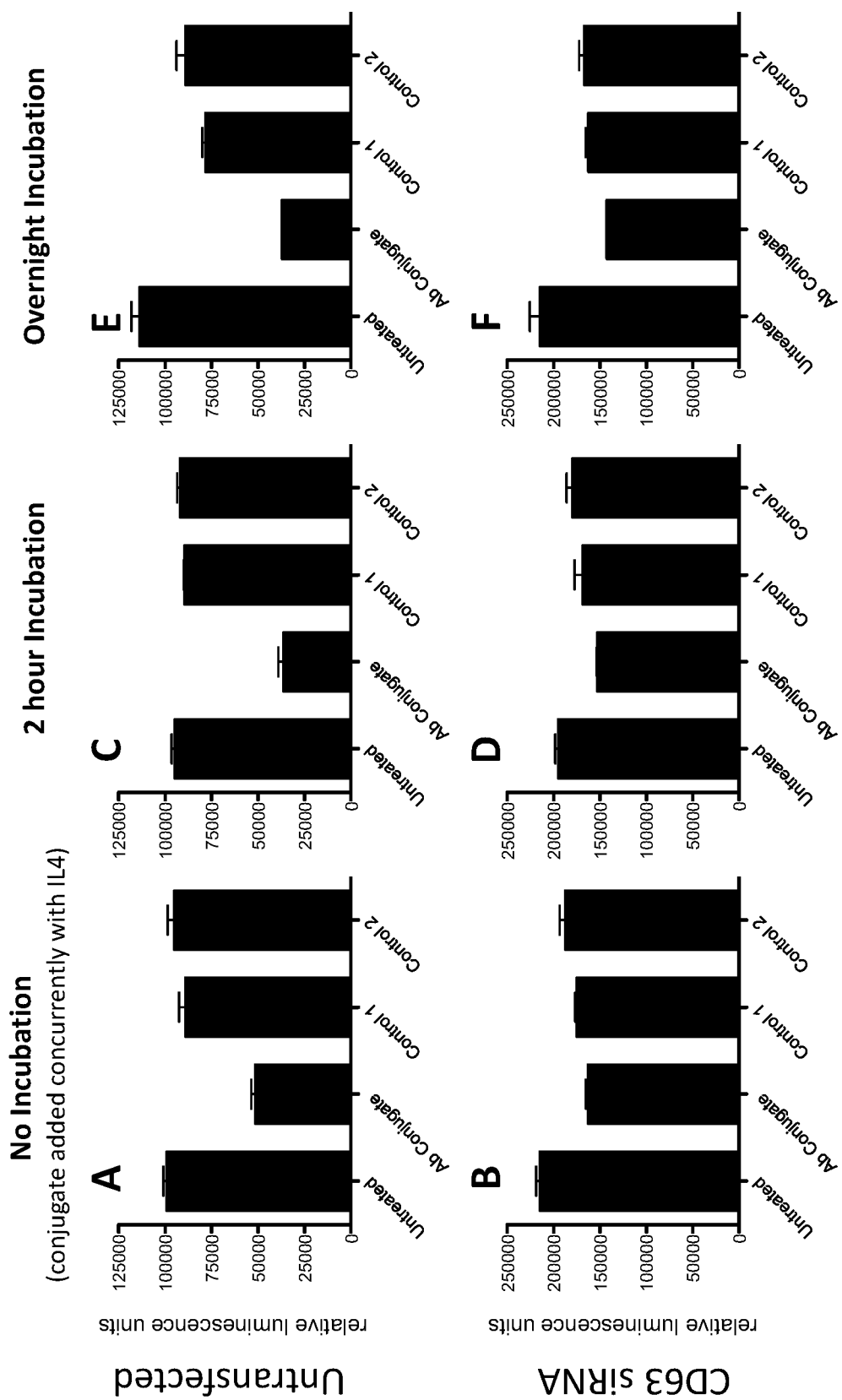
Figure 6:
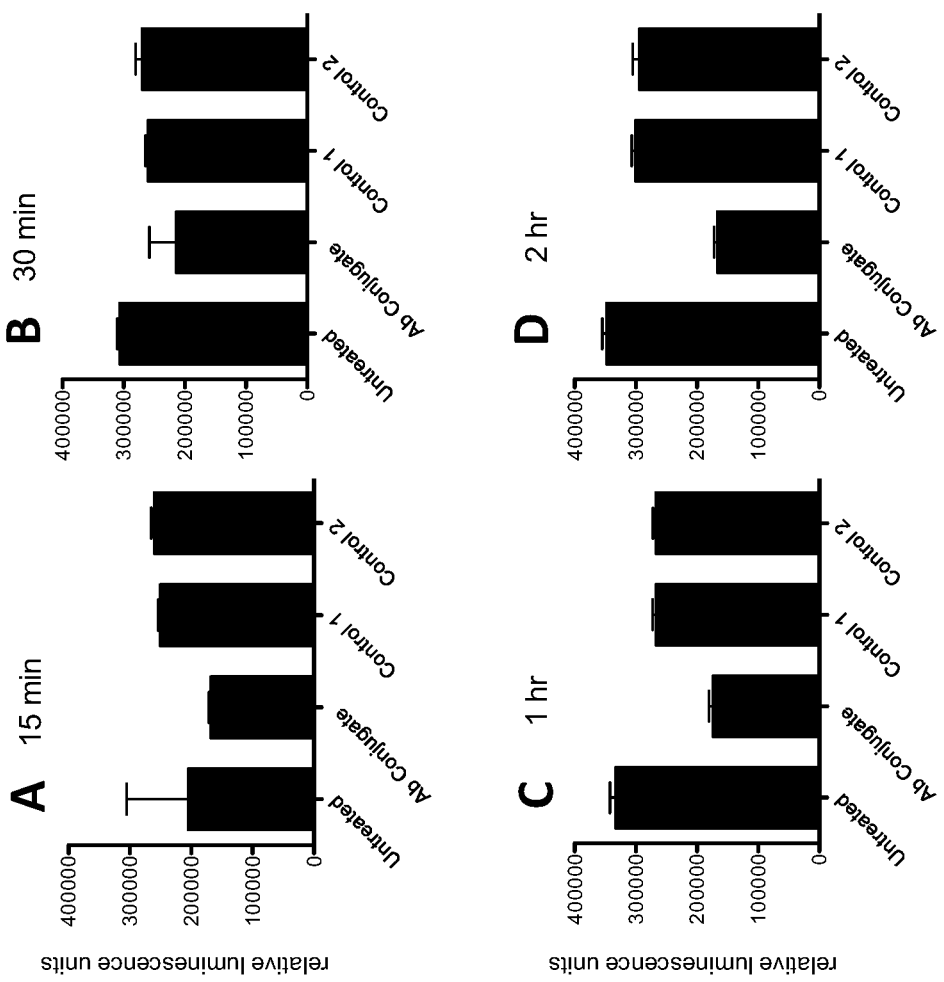

FIG. 5 shows the results of an experiment carried out in a similar manner as the experiments shown in FIGS. 3 and 4, except that the reporter cells were incubated with the multispecific antigen binding protein ("Ab conjugate") or control constructs ("control 1" and "control 2") for 2 hours or overnight prior to the addition of IL-4 ligand. FIGS. 5A, 5C and 5E are bar graphs that represent the results of experiments conducted in cells expressing normal levels of CD63 ("untransfected"), while FIGS. 5B, 5D and 5F are bar graphs represents the results of experiments conducted in cells in which CD63 expression was significantly reduced in the reporter cell line by an siRNA directed against CD63.

FIGS. 6A-D show the results of an experiment carried out in a similar manner as the experiments shown in FIGS. 3 and 4, except that the reporter cells were incubated with the anti-IL-4R/anti-CD63 multispecific antigen binding protein ("Ab conjugate") or control constructs ("control 1" and "control 2") for 15 minutes, 30 minutes, 1 hour or 2 hours prior to the addition of IL-4 ligand.

Figure 7:
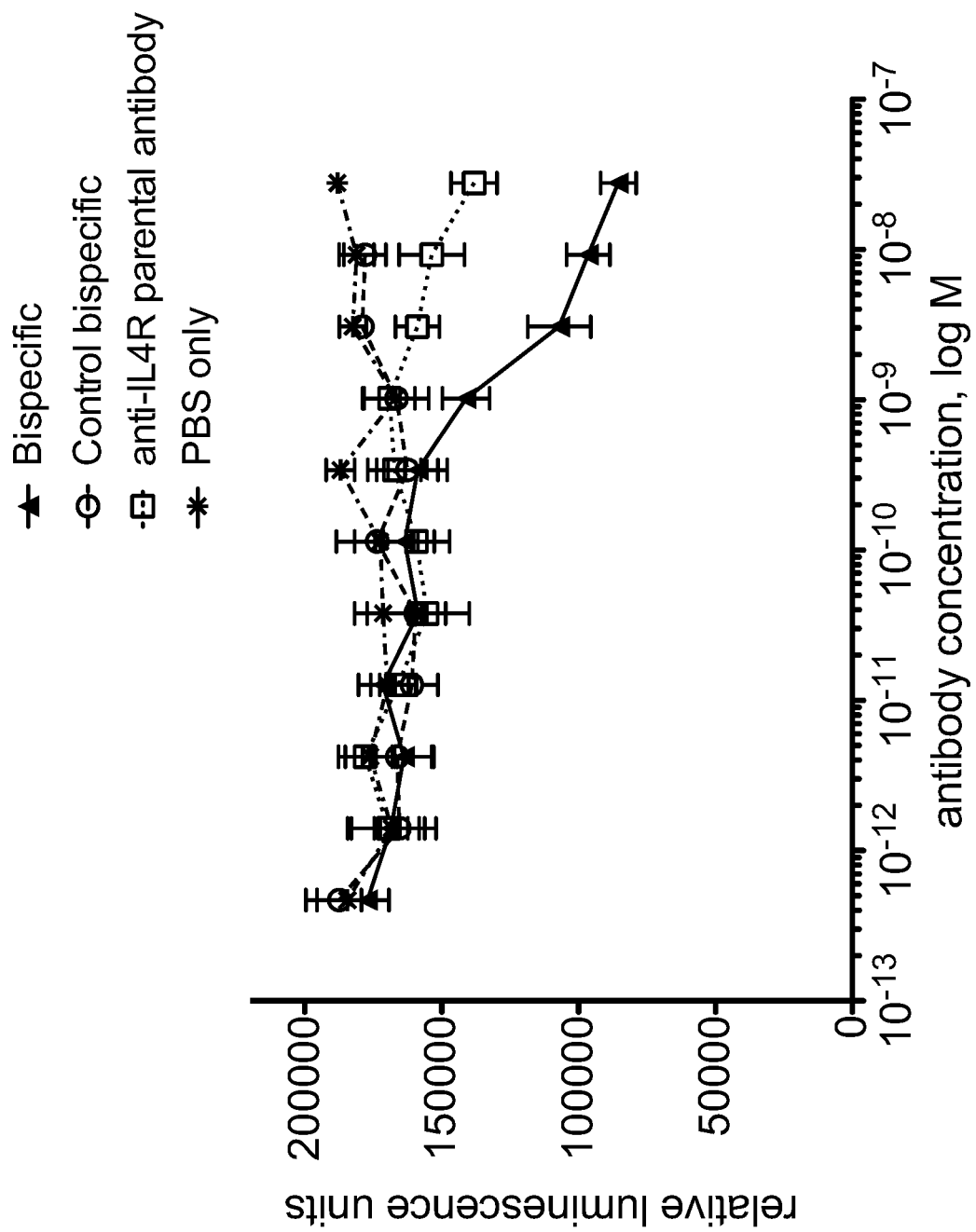

FIG. 7 shows the results of an experiment in which Stat6-luc reporter cells were treated with 10 pM IL-4 in the presence of various dilutions of an anti-IL-4R×anti-CD63 bispecific antibody ("bispecific"), or control constructs (anti-IL-4R monospecific, or mock bispecific that only binds IL-4R).

Figure 8:
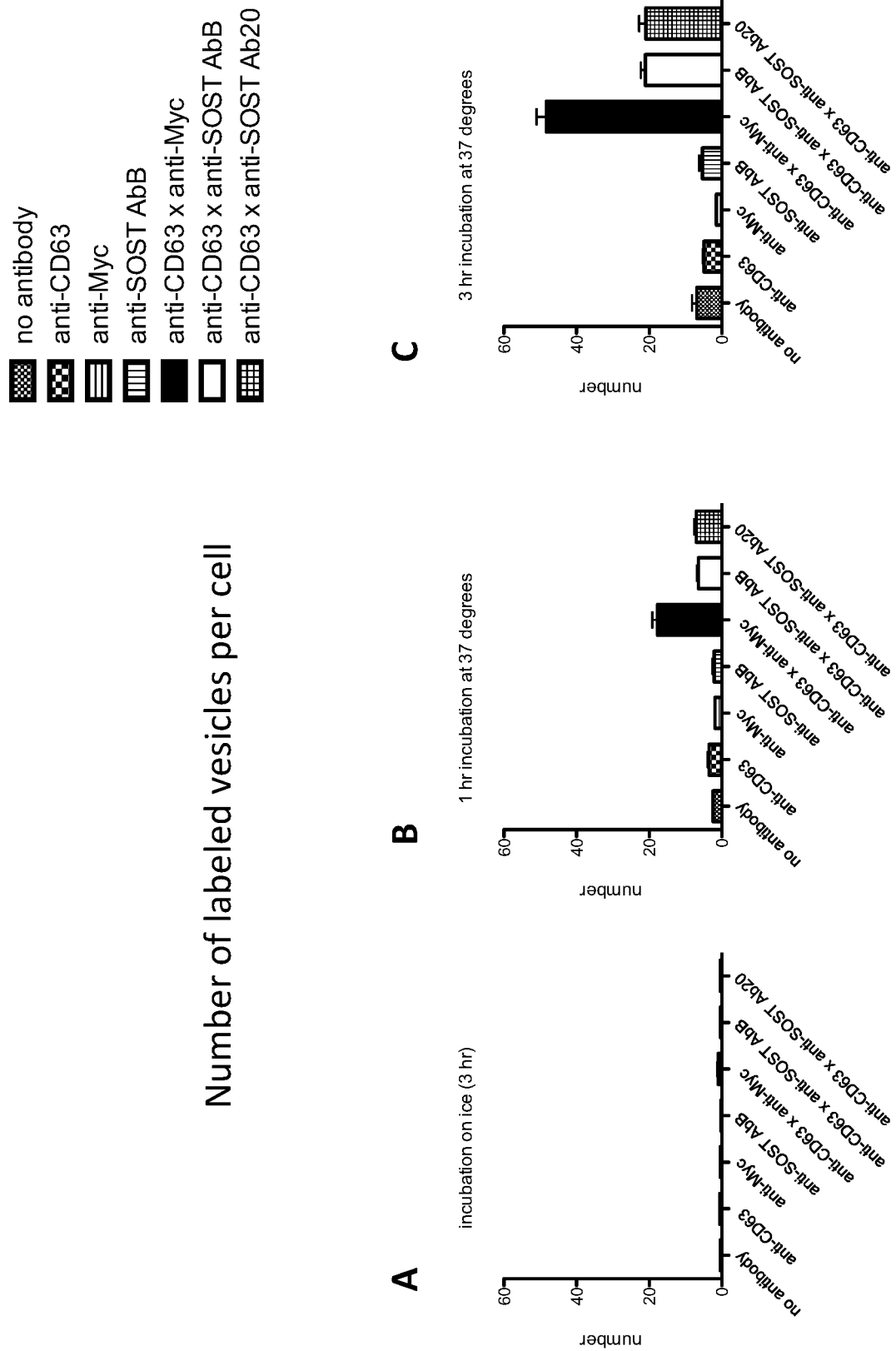

FIG. 8 shows the results of experiments in which HEK293 cells were treated with a SOST construct labeled with a myc tag and a pH-sensitive label (that produces a fluorescent signal at low pH), along with the various mono-specific and bispecific antibodies as shown. Results are expressed in terms of number of fluorescent spots (i.e., labeled vesicles) per cell. Panel 8A shows the results following incubation on ice for 3 hours, panel 8B shows the results following 1 hour incubation at 37° C., and panel 8C shows the results following 3 hours incubation at 37° C.

Figure 9:
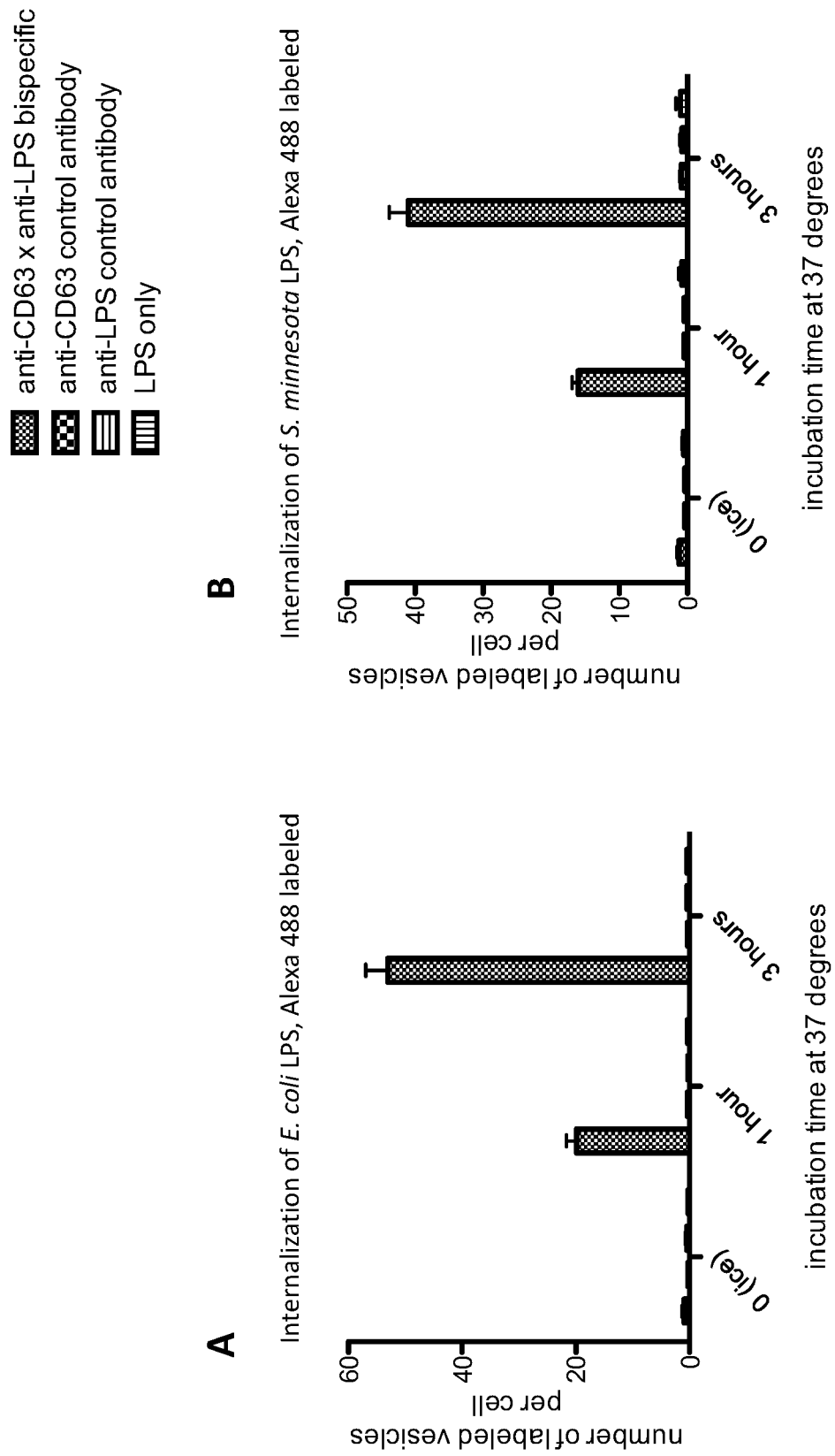

FIG. 9 shows the results of experiments in which HEK293 cells were treated with fluorescently-labeled lipopolysaccharide (LPS) from *E. coli* (Panel 9A) or *S. minnesota* (Panel 9B), along with an anti-CD63×anti-LPS bispecific antibody, control antibodies, or LPS only, for various times, followed by quenching of non-internalized (i.e., surface bound) fluorophore. Fluorescent signal therefore reflects internalized LPS under the various conditions shown. Results are expressed in terms of number of fluorescent spots (i.e., labeled vesicles) per cell.

Figure 10:
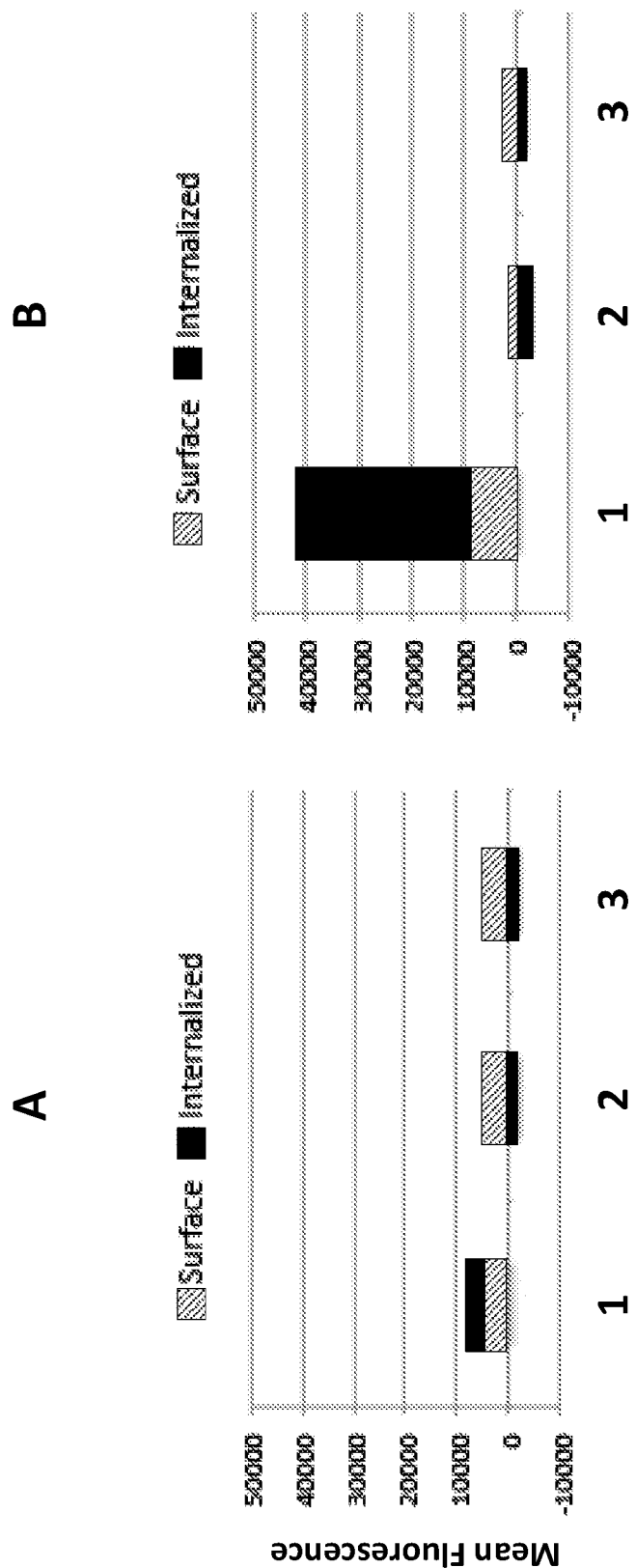

FIG. 10 shows the mean fluorescence in arbitrary units from Alexa488 labeled FelD1-mycv-myc-his. Blue histograms depict cell surface label. Red histograms depict internalized label. Group 1 on the X-axis represents cells treated with anti-HLA-B×anti-FelD1 bispecific antibody; group 2 represents cells treated with anti-HLA-B parental bivalent monospecific antibody; group 3 represents treatment with IgG isotype controls. Panel 10A shows binding and internalization of FelD1-mmh-488 by C1Rneo B-lymphoblastoid cells that do not express MHC1. Panel 10B shows binding and internalization of FelD1-mmh-488 by C1Rneo B-lymphoblastoid cells that express MHC1.

Figure 11:
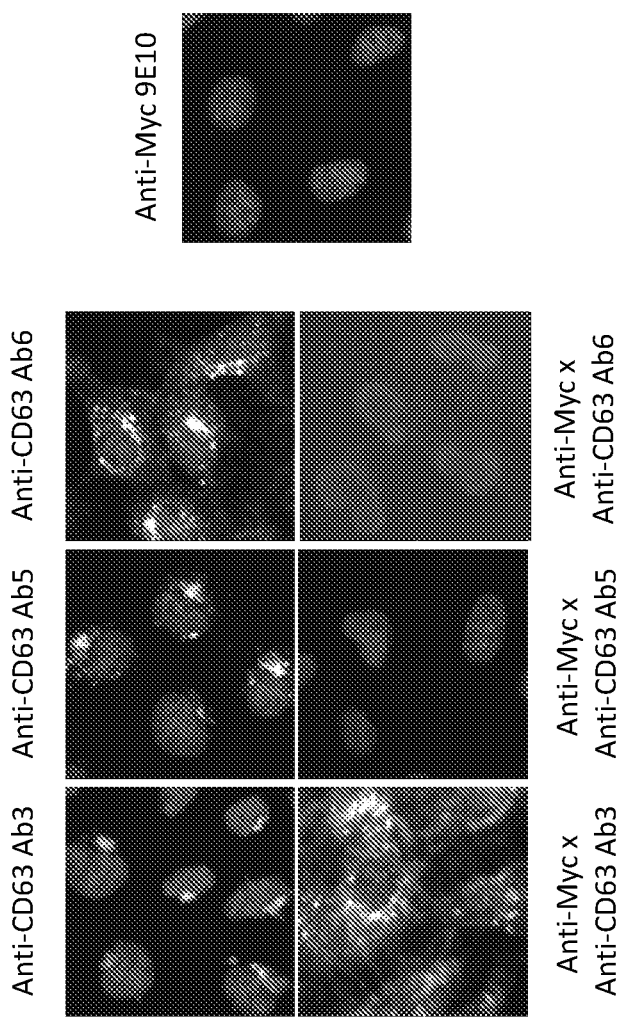

FIG. 11 shows micrographs of HEK293 cells stained with DAPI (blue nuclei) and anti-human IgG secondary Fab Alexa® 647 (green).

Figure 12:
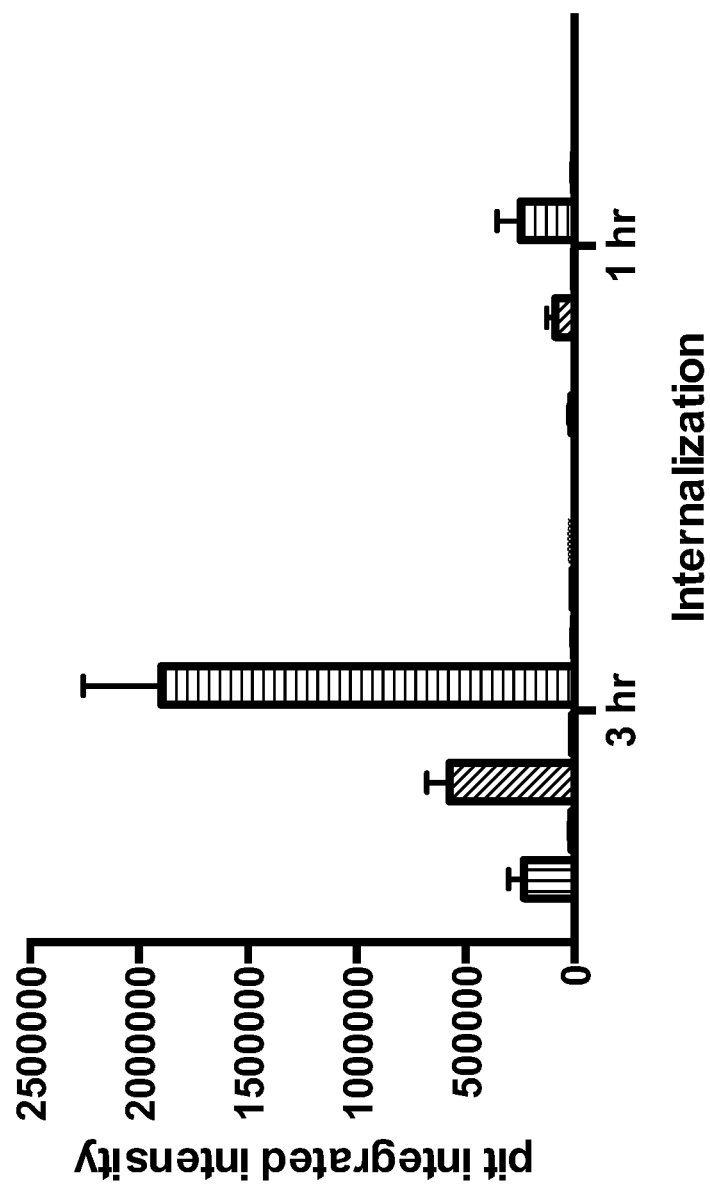

FIG. 12 is a histogram depicting pHrodo®-hHJV-mmh uptake into HEK293 cells. Y-axis depicts pit integrated intensity (arbitrary units) of pHrodo® signal. At the X-axis, cells incubated for 1 hour and for 3 hours are depicted. Anti-HJV 1×anti-CD63 MS-ABP is represented by bars filled with vertical lines. Anti-HJV 2×anti-CD63 MS-ABP is represented by bars filled with diagonal lines. Anti-Myc× anti-CD63 MS-ABP is represented by bars filled with horizontal lines.

DETAILED DESCRIPTION

This invention is not limited to particular methods and experimental conditions described, as such methods and conditions may vary. The terminology used herein is for the purpose of describing particular embodiments only, and is not intended to be limiting, since the scope of the invention is limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, a subset of exemplar methods and materials are now described. All patents, applications and non-patent publications mentioned in this specification are incorporated herein by reference in their entireties.

Multispecific Antigen-Binding Molecules

The invention provides multispecific antigen binding molecules comprising a first antigen-binding domain (also referred to herein as "D1"), and a second antigen-binding domain (also referred to herein as "D2"). D1 and D2 each bind different molecules. D1 specifically binds a "target molecule". The target molecule is also referred to herein as "T". D2 specifically binds an "internalizing effector protein", which includes "destroyer protein". The internalizing effector protein is also referred to herein as "E". According to the present invention, the binding of both T and E by the multispecific antigen-binding molecule attenuates the activity of T to a greater extent than the binding of T by D1 alone. Here, the multispecific antigen-binding molecule is capable of contacting both a target molecule (T) and an internalizing effector protein (E) for at least some period of time under physiologically relevant conditions to facilitate the physical linkage between T and E. The binding of T to D1 individually, or E to D2 individually may be a low affinity binding interaction. However, the combined effect of D1-T binding and D2-E binding leads to a high avidity interaction. Such high avidity interaction may create cell surface clustering and enhance cellular uptake and subsequent destruction of the target. Binding of the multispecific antigen-binding molecule to the T and E components may be sequential and/or cooperative; e.g., the multispecific antigen-binding molecule may first bind T (wherein D1-T has a lower kD and then bind E, or it may first bind E first and then bind T. In any event, so long as T and E are both bound by the multispecific antigen-binding molecule for some period of time (regardless of the sequential order of binding), the multispecific antigen-binding molecule will be deemed to bind both T and E for purposes of the present disclosure. The enhanced inactivation of T is facilitated by the internalization and degradative routing of T within a cell due to its physical linkage to E. The multispecific antigen-binding molecules of the present invention are thus useful for inactivating, reducing the activity of, or reducing the extracellular concentration of a target molecule without directly blocking or antagonizing the function of the target molecule.

According to the present invention, a multispecific antigen-binding molecule can be a single multifunctional polypeptide, or it can be a multimeric complex of two or more polypeptides that are covalently or non-covalently associated with one another, such as e.g., a bispecific antibody. Any antigen binding construct, which has the ability bind a T and an E molecule, is regarded as a multispecific antigen-binding molecule. Any of the multispecific antigen-binding molecules of the invention, or variants thereof, may be constructed using standard molecular biological techniques (e.g., recombinant DNA and protein expression technology). Effective binding domains of the multispecific antigen-binding can be selected individually by applying the method described herein. Likewise, both binding domains can be selected by the disclosed method to produce an effective multispecific antigen-binding protein.

Antigen-Binding Domains

The multispecific antigen-binding molecules of the present invention comprise at least two separate antigen-binding domains (D1 and D2). As used herein, the expression "antigen-binding domain" means any peptide, polypeptide, nucleic acid molecule, scaffold-type molecule, peptide display molecule, or polypeptide-containing construct that is capable of specifically binding a particular antigen of interest. The term "specifically binds" or the like, as used herein, means that the antigen-binding domain forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another.

Exemplary categories of antigen-binding domains that can be used in the context of the present invention include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]), and aptamers or portions thereof.

In certain embodiments in which the target molecule or the internalizing effector protein is a receptor molecule, an "antigen-binding domain," for purposes of the present invention, may comprise or consist of a ligand or portion of a ligand that is specific for the receptor. For example, if the target molecule (T) is IL-4R, the D1 component of the multispecific antigen-binding molecule may comprise the IL-4 ligand or a portion of the IL-4 ligand that is capable of specifically interacting with IL-4R; or if the internalizing effector protein (E) is transferrin receptor, the D2 component of the multispecific antigen-binding molecule may comprise transferrin or a portion of transferrin that is capable of specifically interacting with the transferrin receptor.

In certain embodiments in which the target molecule or the internalizing effector protein is a ligand that is specifically recognized by a particular receptor (e.g., a soluble target molecule), an "antigen-binding domain" for purposes of the present invention may comprise or consist of the receptor or a ligand-binding portion of the receptor. For example, if the target molecule (T) is IL-6, the D1 component of the multispecific antigen-binding molecule may comprise the ligand-binding domain of the IL-6 receptor; or if the internalizing effector protein (E) is an indirectly internalized protein (as that term is defined elsewhere herein), the D2 component of the multispecific antigen-binding molecule may comprise a ligand-binding domain of a receptor specific for E.

Methods for determining whether two molecules specifically bind one another are well known in the art and include, for example, equilibrium dialysis, surface plasmon resonance, and the like. For example, an antigen-binding domain, as used in the context of the present invention, includes polypeptides that bind a particular antigen (e.g., a target molecule [T] or an internalizing effector protein [E]) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

The term "avidity", as used herein, means the cumulative strength of multiple individual binding interactions, wherein one or more binding interactions may have low individual affinity. The combination of multiple low affinity interactions creates a complex that is stable and where the cumulative interaction has high "avidity."

Similarly, a high avidity ternary complex may form through "cooperativity." Here, a protein may bind two or more ligands in which each individual binding relationship has a different affinity. When the protein binds the high affinity ligand first, the three dimensional structure or degrees of freedom of movement changes such that the second ligand binds with greater affinity then in the absence of the first ligand, and so on. Cooperativity allows individual low affinity binding events to increase in affinity as each ligand binds to the protein in a cascade-like fashion. For example, the binding of a soluble multispecific antigen-binding protein to a higher affinity membrane protein increases the likelihood of subsequent binding to a low affinity membrane protein and overall stability of the complex.

Similarly, clustering of receptors at the cell membrane enhances endocytosis by increasing the likelihood of receptor and ligand binding to trafficking proteins. Also via cooperativity, a low affinity binding domain of a multispecific antigen-binding protein may increase in its likelihood and strength of binding to a cell surface receptor after a high affinity binding domain of that same multispecific antigen-binding domain had bound its soluble target to form a multimeric (e.g., tetrameric) complex.

Thus in some embodiments, the D2 component may bind with low affinity to the internalizing effector protein "E". Thus, the multispecific antigen-binding molecule will preferentially target cells that express the target antigen. As used herein, "low affinity" binding means that the binding affinity of the D2 component for the internalizing effector protein (E) is at least 10% weaker (e.g., 15% weaker, 25% weaker, 50% weaker, 75% weaker, 90% weaker, etc.) than the binding affinity of the D1 component for the target molecule (T). In certain embodiments, "low affinity" binding means that the D2 component interacts with the internalizing effector protein (E) with a $K_D$ of greater than about 10 nM to about 1 μM, as measured in a surface plasmon resonance assay at about 25° C.

Antibodies and Antigen-Binding Fragments of Antibodies

As indicated above, an "antigen-binding domain" (D1 and/or D2) can comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., T or E). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies of the invention (or antigen-binding portion thereof) may be identical to the human germline sequences, or may be naturally or artificially modified. An amino acid consensus sequence may be defined based on a side-by-side analysis of two or more CDRs.

The D1 and/or D2 components of the multispecific antigen-binding molecules of the present invention may comprise or consist of antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein. ScFv molecules include polypeptide chains containing an immunoglobulin light chain variable region and an immunoglobulin heavy chain domain usually connected with a short linker peptide (10-25 amino acids). ScFv molecules can be combined to form tandem di-scFvs, diabodies, tandem tri-scFvs, and tri(a)bodies. The making and using of scFvs are discussed inter alia in Hilliger et al., PNAS 1993 Jul. 15; 90(14): 64444-6448.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The multispecific antigen-binding molecules of the present invention may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The multispecific antigen-binding molecules of the present invention may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Bispecific Antibodies

According to certain embodiments, the multispecific antigen-binding molecules of the invention are bispecific antibodies; e.g., bispecific antibodies comprising an antigen-binding arm that specifically binds a target molecule (T) and an antigen-binding arm that specifically binds an internalizing effector protein (E). Methods for making bispecific antibodies are known in the art and may be used to construct multispecific antigen-binding molecules of the present invention. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats).

In some embodiments, the scFv-based bispecific antibody contains an scFv polypeptide chain that binds to a target molecule (T). In other embodiments, the scFv-based bispecific antibody contains an scFv polypeptide chain that binds to a destroyer molecule or other internalizing effector domain protein (E). In a preferred embodiments, the scFv-based bispecific antibody contains an scFv polypeptide chain that binds to a target molecule (T) and another scFv polypeptide chain that binds to a destroyer molecule or other internalizing effector domain protein (E).

Multimerizing Components

The multispecific antigen-binding molecules of the present invention, in certain embodiments, may also comprise one or more multimerizing component(s). The multimerizing components can function to maintain the association between the antigen-binding domains (D1 and D2). As used herein, a "multimerizing component" is any macromolecule, protein, polypeptide, peptide, or amino acid that has the ability to associate with a second multimerizing component of the same or similar structure or constitution. For example, a multimerizing component may be a polypeptide comprising an immunoglobulin $C_H3$ domain. A non-limiting example of a multimerizing component is an Fc portion of an immunoglobulin, e.g., an Fc domain of an IgG selected from the isotypes IgG1, IgG2, IgG3, and IgG4, as well as any allotype within each isotype group. In certain embodiments, the multimerizing component is an Fc fragment or an amino acid sequence of 1 to about 200 amino acids in length containing at least one cysteine residues. In other embodiments, the multimerizing component is a cysteine residue, or a short cysteine-containing peptide. Other multimerizing domains include peptides or polypeptides comprising or consisting of a leucine zipper, a helix-loop motif, or a coiled-coil motif.

In certain embodiments, the multispecific antigen-binding molecules of the present invention comprise two multimerizing domains, M1 and M2, wherein D1 is attached to M1 and D2 is attached to M2, and wherein the association of M1 with M2 facilitates the physical linkage of D1 and D2 to one another in a single multispecific antigen-binding molecule. In certain embodiments, M1 and M2 are identical to one another. For example, M1 can be an Fc domain having a particular amino acid sequence, and M2 is an Fc domain with the same amino acid sequence as M1. Alternatively, M1 and M2 may differ from one another at one or more amino acid position. For example, M1 may comprise a first immunoglobulin (Ig) $C_H3$ domain and M2 may comprise a second Ig $C_H3$ domain, wherein the first and second Ig $C_H3$ domains differ from one another by at least one amino acid, and wherein at least one amino acid difference reduces binding of the targeting construct to Protein A as compared to a reference construct having identical M1 and M2 sequences. In one embodiment, the Ig $C_H3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

Internalizing Effector Proteins (E)

In the context of the present invention, the D2 component of the multispecific antigen-binding molecule specifically binds an internalizing effector protein ("E"). An internalizing effector protein is a protein that is capable of being internalized into a cell or that otherwise participates in or contributes to retrograde membrane trafficking. In some cases, the internalization effector directly or indirectly traffics the target to endosomes and vesicles of increasingly lower pH, culminating in the lysosome, wherein the target is degraded. Here, the internalization effector "E" may be referred to as a "destroyer" molecule or protein. In some instances, the internalizing effector protein is a protein that undergoes transcytosis; that is, the protein is internalized on one side of a cell and transported to the other side of the cell (e.g., apical-to-basal). In many embodiments, the internalizing effector protein is a cell surface-expressed protein or a soluble extracellular protein. However, the present invention also contemplates embodiments in which the internalizing effector protein is expressed within an intracellular compartment such as the endosome, endoplasmic reticulum, Golgi, lysosome, etc. For example, proteins involved in retrograde membrane trafficking (e.g., pathways from early/recycling endosomes to the trans-Golgi network) may serve as internalizing effector proteins in various embodiments of the present invention. In any event, the binding of D2 to an internalizing effector protein causes the entire multispecific antigen-binding molecule, and any molecules associated therewith (e.g., a target molecule bound by D1), to also become internalized into the cell. As explained below, internalizing effector proteins include proteins that are directly internalized into a cell, as well as proteins that are indirectly internalized into a cell.

Internalizing effector proteins that are directly internalized into a cell include membrane-associated molecules with at least one extracellular domain (e.g., transmembrane proteins, GPI-anchored proteins, etc.), which undergo cellular internalization, and are preferably processed via an intracellular degradative and/or recycling pathway. Specific non-limiting examples of internalizing effector proteins that are directly internalized into a cell include, e.g., proprotein convertase subtilisin/kexin type 9 (PCSK9), CD63, MHC-I (e.g., HLA-B27), Kremen-1, Kremen-2, LRP5, LRP6, LRP8, transferrin receptor, LDL-receptor, LDL-related protein 1 receptor, ASGR1, ASGR2, amyloid precursor protein-like protein-2 (APLP2), apelin receptor (APLNR), MAL (Myelin And Lymphocyte protein, a.k.a. VIP17), IGF2R, vacuolar-type $H^+$ ATPase, diphtheria toxin receptor, folate receptor, glutamate receptors, glutathione receptor, leptin receptors, scavenger receptors (e.g., SCARA1-5, SCARB1-3, CD36), etc.

In embodiments in which E is a directly internalized effector protein, the D2 component of the multispecific antigen-binding molecule can be, e.g., an antibody or antigen-binding fragment of an antibody that specifically binds E, or a ligand or portion of a ligand that specifically interacts with the effector protein. For example, if E is Kremen-1 or Kremen-2, the D2 component can comprise or consist of a Kremen ligand (e.g., DKK1) or Kremen-binding portion thereof. As another example, if E is a receptor molecule such as ASGR1, the D2 component can comprise or consist of a ligand specific for the receptor (e.g., asialoorosomucoid [ASOR] or Beta-GalNAc) or a receptor-binding portion thereof. In still another example, if E is a receptor molecule such as APLP2 or LDLR, the D2 component can comprise or consist of a ligand specific for the receptor (e.g., PCSK9) or a receptor-binding portion thereof.

Internalizing effector proteins that are indirectly internalized into a cell include proteins and polypeptides that do not internalize on their own, but become internalized into a cell after binding to or otherwise associating with a second protein or polypeptide that is directly internalized into the cell. Proteins that are indirectly internalized into a cell include, e.g., soluble ligands that are capable of binding to an internalizing cell surface-expressed receptor molecule. A non-limiting example of a soluble ligand that is (indirectly) internalized into a cell via its interaction with an internalizing cell surface-expressed receptor molecule is transferrin. Another example is PCSK9. In embodiments wherein E is transferrin or PCSK9 (or another indirectly internalized protein), the binding of D2 to E, and the interaction of E with transferrin receptor or APLP2/LDLR (or another internalizing cell-surface expressed receptor molecule), causes the entire multispecific antigen-binding molecule, and any molecules associated therewith (e.g., a target molecule bound by D1), to become internalized into the cell concurrent with the internalization of E and its binding partner.

In embodiments in which E is an indirectly internalized effector protein such as a soluble ligand, the D2 component of the multispecific antigen-binding molecule can be, e.g., an antibody or antigen-binding fragment of an antibody that specifically binds E, or a receptor or portion of a receptor that specifically interacts with the soluble effector protein.

For example, if E is a cytokine, the D2 component can comprise or consist of the corresponding cytokine receptor or ligand-binding portion thereof.

Target Molecules (T)

In the context of the present invention, the D1 component of the multispecific antigen-binding molecule specifically binds a target molecule ("T"). A target molecule is any protein, polypeptide, or other macromolecule whose activity or extracellular concentration is desired to be attenuated, reduced or eliminated. In many instances, the target molecule to which D1 binds is a protein or polypeptide [i.e., a "target protein"]; however, the present invention also includes embodiments wherein the target molecule ("T") is a carbohydrate, glycoprotein, lipid, lipoprotein, lipopolysaccharide, or other non-protein polymer or molecule to which D1 binds. According to the present invention, T can be a cell surface-expressed target protein or a soluble target protein. Target binding by the multispecific antigen-binding molecule may take place in an extracellular or cell surface context. In certain embodiments, however, the multispecific antigen-binding molecule binds a target molecule inside the cell, for example within an intracellular component such as the endoplasmic reticulum, Golgi, endosome, lysosome, etc.

In many embodiments, the target molecule is a therapeutically relevant molecule. Non-limiting examples of therapeutically relevant targets include activin receptor-like kinase 1, adenocarcinoma antigen, ACVR2b, AGS-22M6, alpha-fetoprotein, angiopoietin 2, angioepoietin 3, anthrax toxin, AOC3, B-lymphoma cell antigen, B7-H3, *Bacillus anthracis*, BAFF, C—X—C chemokine receptor type 4, C242, C5, CA-125, carbonic anhydrase 9, cardiac myosin, CCL11, CCR4, CCR5, CD2, CD3, CD4, CD6, CD11/CD18, CD11a, CD15, CD19, CD20, CD22, CD23, CD25, CD27, CD28, CD30, CD33, CD37, CD38, CD40, CD41, CD44, CD51, CD52, CD56, CD70, CD74, CD79, CD80, CD125, CD140, CD147, CD152, CD154, CD200, CD221, CD274, CEA, CFD, ch4D5, CLDN18.2, *Clostridium difficile*, CSF1R, CSF2, CTLA-4, cytomegalovirus, dabigatran, DLL4, DPP4, DRS, shiga toxin, EGFL7, EGFR, endotoxin, EpCAM, episialin, ERBB3, *Escherichia coli*, F protein of respiratory syncytial virus, FAP, fibrin, fibronectin, folate receptor, frizzled receptor, ganglioside GD2, ganglioside GD3, glypican 3, GMCSF, GPNMB, GDF8, GUCY2C, hemagglutinin, hepatitis B surface antigen, HER1, HER2, HGF, HHGFR, histone, HIV-1, HLA-DR, HNGF, Hsp90, IFN-α, IFN-γ, IFN-α/β receptor, IgE, IGF-1R, IGF-1, IGHE, IL-1, IL-4, IL-4R, IL-5, IL-6, IL-6R, IL-9, IL-12, IL-13, IL-17, IL-22, IL-23, ILGF2, ILGF-1R, influenza A hemagglutinin, integrin α4, integrin α4β7, integrin α5β1, integrin α7β7, integrin αIIbβ3, integrin αvβ3, interferon gamma-induced protein, ITGA2, KIR2D, L-selectin, LINGO-1, lipoteichoic acid, LOXL2, LTA, MCP-1, mesothelin, MIF, MS4A1, MSLN, MUC1, mucin cancer antigen, myelin-associated glycoprotein, myostatin, N-glycolyl-neuraminic acid, NCA-90, neural apoptosis-regulated proteinase 1, NGF, NOGO-A, notch receptor, NRP1, *Oryctolagus cuniculus*, OX-40, oxLDL, PCSK9, PD-1, PDCD1, PDGF-Rα, PDGF-Rβ, phosphate-sodium co-transporter, phosphatidylserine, prostatic carcinoma cells, *Pseudomonas aeruginosa*, rabies virus glycoprotein, RANKL, respiratory syncytial virus, RHD, Rhesus factor, RON, RTN4, sclerostin, SDC1, selectin P, SLAM7, SOST, sphingosine-1-phosphate, *Staphylococcus aureus*, STEAP1, T-cell receptor, TAG-72, TEM1, tenascin C, TFP1, TGF-β1, TGF-β2, TGF-β, TNF-α, TRAIL-R1, TRAIL-R2, tumor antigen CTAA16.88, tumor-associated calcium signal transducer 2, TWEAK receptor, VEGF-A, VEGFR-1, VEGFR-2, vimentin, VWF, and the like.

Examples of cell surface-expressed target molecules include cell surface-expressed receptors, membrane-bound ligands, ion channels, and any other monomeric or multimeric polypeptide component with an extracellular portion that is attached to or associated with a cell membrane. Non-limiting, exemplary cell surface-expressed target molecules that may be targeted by the multispecific antigen-binding molecule of the present invention include, e.g., cytokine receptors (e.g., receptors for IL-1, IL-4, IL-6, IL-13, IL-22, IL-25, IL-33, etc.), as well as cell surface targets including other type 1 transmembrane receptors such as PRLR, G-protein coupled receptors such as GCGR, ion channels such as Nav1.7, ASIC1 or ASIC2, non-receptor surface proteins such as MHC-I (e.g., HLA-B27), and the like.

In embodiments in which T is a cell surface-expressed target protein, the D1 component of the multispecific antigen-binding molecule can be, e.g., an antibody or antigen-binding fragment of an antibody that specifically binds T, or a ligand or portion of a ligand that specifically interacts with the cell surface-expressed target protein. For example, if T is IL-4R, the D1 component can comprise or consist of IL-4 or a receptor-binding portion thereof.

Examples of soluble target molecules include cytokines, growth factors, and other ligands and signaling proteins. Non-limiting exemplary soluble target protein that may be targeted by the multispecific antigen-binding molecule of the present invention include, e.g., IL-1, IL-4, IL-6, IL-13, IL-22, IL-25, IL-33, SOST, DKK1, etc. Soluble targets molecules also include, e.g., non-human target molecules such as allergens (e.g., Fel D1, Betv1, CryJ1), pathogens (e.g., *Candida albicans, S. aureus*, etc.), and pathogenic molecules (e.g., lipopolysaccharide [LPS], lipotechoic acid [LTA], Protein A., toxins, etc.). In embodiments in which T is a soluble target molecule, the D1 component of the multispecific antigen-binding molecule can be, e.g., an antibody or antigen-binding fragment of an antibody that specifically binds T, or a receptor or portion of a receptor that specifically interacts with the soluble target molecule. For example, if T is IL-4, the D1 component can comprise or consist of IL-4R or a ligand-binding portion thereof.

Target molecules also include tumor-associated antigens. Non-limiting examples of specific tumor-associated antigens include, e.g., AFP, ALK, BAGE proteins, β-catenin, brc-abl, BRCA1, BORIS, CA9, carbonic anhydrase IX, caspase-8, CD40, CDK4, CEA, CTLA4, cyclin-B1, CYP1B1, EGFR, EGFRvIII, ErbB2/Her2, ErbB3, ErbB4, ETV6-AML, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, survivin, TAG-72, TGF-β, TMPRSS2, Tn, TRP-1, TRP-2, tyrosinase, and uroplakin-3.

pH-Dependent Binding

The present invention provides multispecific antigen-binding molecules comprising a first antigen-binding domain (D1) and a second antigen-binding domain (D2), wherein one or both of the antigen-binding domains (D1 and/or D2) binds its antigen (T or E) in a pH-dependent manner. For example, an antigen-binding domain (D1 and/or D2) may exhibit reduced binding to its antigen at acidic pH as compared to neutral pH. Alternatively, an antigen-binding domain (D1 and/or D2) may exhibit enhanced binding to its antigen at acidic pH as compared to neutral pH. Antigen-binding domains with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antigen-binding domains with pH-dependent characteristics. For example, by substituting one or more amino acid of an antigen-binding domain (e.g., within a CDR) with a histidine residue, an antigen-binding domain with reduced antigen-binding at acidic pH relative to neutral pH may be obtained.

In certain embodiments, the present invention includes multispecific antigen-binding molecules comprising a D1 and/or D2 component that binds its respective antigen (T or E) at acidic pH with a $K_D$ that is at least about 3, 5, 10, 11, 12, 13, 14, 15, 16, 17, 18, 19, 20, 25, 30, 35, 40, 45, 50, 55, 60, 65, 70, 75, 80, 85, 90, 95, 100, or more times greater than the $K_D$ of the D1 and/or D2 component for binding to its respective antigen at neutral pH. pH dependent binding may also be expressed in terms of the t½ of the antigen-binding domain for its antigen at acidic pH compared to neutral pH. For example, the present invention includes multispecific antigen-binding molecules comprising a D1 and/or D2 component that binds its respective antigen (T or E) at acidic pH with a t½ that is at least about 5, 6, 7, 8, 9, 10, 15, 20, 25, 30, 35, 40, 45, 50, 55, 60, or more times shorter than the t½ of the D1 and/or D2 component for binding to its respective antigen at neutral pH.

Multispecific antigen-binding molecules of the present invention that comprise a D1 and/or D2 component with reduced antigen binding at acidic pH as compared to neutral pH, when administered to animal subjects, may in certain embodiments exhibit slower clearance from circulation as compared to comparable molecules that do not exhibit pH-dependent binding characteristics. According to this aspect of the invention, multispecific antigen-binding molecules with reduced antigen binding to either T and/or E at acidic pH as compared to neutral pH are provided which exhibit at least 2 times slower clearance from circulation relative to comparable antigen-binding molecules that do not possess reduced antigen binding at acidic pH as compared to neutral pH. Clearance rate can be expressed in terms of the half-life of the antibody, wherein a slower clearance correlates with a longer half-life.

As used herein, the expression "acidic pH" means a pH of 6.0 or less. The expression "acidic pH" includes pH values of about 6.0, 5.95, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Attenuation of Target Molecule Activity

The binding of both a target molecule (T) and an internalizing effector protein (E) by a multispecific antigen-binding molecule to form a ternary or larger complex attenuates the activity of T to a greater extent than the binding of T by the first antigen-binding domain (D1) component of the multispecific antigen-binding molecule alone. As used herein, the expression "attenuates the activity of T to a greater extent than the binding of T by D1 alone" means that, in an assay in which the activity of T can be measured using cells that express E, the level of T activity measured in the presence of a multispecific antigen-binding molecule is at least 10% lower than the level of T activity measured in the presence of a control construct containing D1 by itself (i.e., not physically linked to the second antigen-binding domain (D2)). For instance, the level of T activity measured in the presence of the multispecific antigen-binding molecule may be about 10%, 15%, 20%, 25%, 30%, 35%, 40%, 45%, 50%, 55%, 60%, 65%, 70%, 75%, 80%, 85%, 90%, 95%, or 100% lower than the level of T activity measured in the presence of a control construct containing D1 by itself.

In some embodiments, the target-binding domain portion of the multispecific antigen-binding protein is or is derived from a target-binding molecule that does not block target activity; but when combined with an effector-binding domain, does affect target activity.

A non-limiting, illustrative assay format for determining whether a multispecific antigen-binding molecule attenuates the activity of a target molecule to a greater extent than the binding of the target molecule by the D1 domain alone is shown in working Examples 1 and 2, herein below. In Example 1, for instance, "T" is the interleukin-4 receptor (IL-4R), and "E" is CD63. The multispecific antigen-binding molecule of Example 1 is a 2-antibody conjugate comprising an anti-IL-4R mAb linked to an anti-CD63 mAb via a streptavidin/biotin linker. Thus, "D1" in this exemplary construct is the antigen-binding domain (HCVR/LCVR pair) of the anti-IL-4R antibody, and "D2" is the antigen-binding domain (HCVR/LCVR pair) of the anti-CD63 antibody. For the experiments of Examples 1 and 2, a cell-based assay format was used that produces a reporter signal when IL-4R activity is stimulated by the addition of exogenous IL-4 ligand. The amount of IL-4-induced reporter activity detected in the presence of the multispecific antigen-binding molecule was compared to the amount of IL-4-induced reporter activity detected in the presence of control constructs containing the anti-IL-4R antibody either connected to an irrelevant control immunoglobulin (control 1), or combined with, but not physically connected to, the anti-CD63 antibody (control 2). The control constructs thus produce the condition in which T is bound by D1 alone (i.e., wherein D1 is not a part of the multispecific antigen-binding molecule per se). If the extent of target molecule activity (represented by the reporter signal) observed in the presence of the multispecific antigen-binding molecule is at least 10% less than the amount of target molecule activity observed in the presence of a control construct comprising the D1 component not physically linked to the D2 component (e.g., control 1 or control 2), then for purposes of the present disclosure, it is concluded that "the simultaneous binding of T and E by the multispecific antigen-binding molecule attenuates the activity of T to a greater extent than the binding of T by D1 alone."

The binding of T by D1 alone may, in some embodiments, result in partial attenuation of the activity of T (as in the case of Example 1 where the treatment of reporter cells with an anti-IL-4R antibody alone [i.e., controls 1 and 2] caused a small level of attenuation of IL-4 signaling relative to untreated cells). In other embodiments, the binding of T by D1 alone will result in no detectable attenuation of the activity of T; that is, the biological activity of T may be unaffected by the binding of T by D1 alone. In any event, however, the simultaneous binding of T and E by a multispecific antigen-binding molecule of the invention will attenuate the activity of T to a greater extent than the binding of T by D1 alone.

Alternative assay formats and variations on the assay format(s) exemplified herein will be apparent to persons of ordinary skill in the art, taking into account the nature of the specific target molecule and effector proteins to which any given multispecific antigen-binding molecule may be directed. Any such format can be used in the context of the present invention to determine whether the simultaneous binding of T and E by a multispecific antigen-binding molecule attenuates the activity of T to a greater extent than the binding of T by D1 alone.

Production and Selection of Effective Binding Domains

The present invention includes processes for making a multispecific antigen-binding protein. As mention above, standard molecular methods can be employed to construct antibodies, fusion proteins, and the like. Some embodiments of the multispecific antigen-binding protein require that the D1 and D2 binding domains function effectively together. By effective, what is meant is the specific binding of the target and the internalization effector to form a ternary or greater complex at the cell surface that is endocytosed. In some embodiments, the complex is targeted to the lysosome, wherein the target is degraded (here internalization effector is a.k.a. destroyer). In some embodiments, the target-binding domain (target paratope) binds the target at an epitope that alone would not block target activity. For example, if the monovalent monospecific antibody or the bivalent monospecific antibody that binds to the target does not block target activity, then that antibody arm comprises a target-binding domain that alone would not block target activity.

An effective internalization effector paratope when alone (as a single paratope) binds E with low affinity and has low to no aggregation effect on E. However, the effective E paratope, when presented as a dimer, trimer, or other multimer, whether as a multisubunit protein, or as part of a macromolecular complex, binds avidly to and stimulates effector aggregation and/or internalization. For example, a bispecific antibody comprising one arm that binds E and another arm that does not bind E will not induce internalization or aggregation of E, generally. However, a bivalent monospecific antibody that binds E (i.e., which has two E paratopes), can promote aggregation and internalization. Such an E-binding arm is an effective internalization effector binding domain of a multispecific antigen-binding domain.

In some embodiments and by way of example, a complex containing two or more E paratopes may be produced by binding a bispecific antibody to a soluble target molecule that dimerizes. Here, the target-specific arm binds one target polypeptide and two target polypeptides form a target dimer or other multimer, leaving two or more internalization effector-specific binding arms free to bind two or more internalization effectors. In other embodiments or examples, two bispecific antibodies are provided, each of which comprise an internalization effector binding arm, one of which comprises a first target paratope that binds to one target epitope, and the other of which comprises a second target paratope that binds to another and non-interfering target epitope. When each antibody binds the same target molecule, two internalization effector binding arms are available. In yet other embodiments or examples, two bispecific antibodies are provided, each of which comprise an internalization effector binding arm, one of which comprises an effector arm that binds one polypeptide of a target complex, and the other of which comprises an effector arm that binds to another polypeptide of the same target complex. When each antibody binds their respective polypeptides of the target complex, two internalization effector binding arms are available.

A multispecific antigen-binding protein (MS-ABP) that effectively destroys a target molecule (or complex incorporating target) can be made or selected using a cell-based assay. In some embodiments in which the target is a soluble protein, an assay cell that expresses the internalization effector (a.k.a. destroyer molecule) is contacted with a MS-ABP and a target molecule (or a fragment of a target molecule, a fusion protein comprising all or part of a target molecule, or a complex containing a target) containing a label. The assay cell is sufficiently incubated to allow the MS-ABP, labeled target, and internalization effector to form a complex and for that complex to be internalized. Label that had been internalized is detected. Those MS-ABPs that promote internalization of label are selected as effective and useful MS-ABPs.

In some embodiments, the MS-ABP is a bispecific antibody, in which one arm comprises the target-binding domain, and the other arm comprises the destroyer-binding domain. For the sake of convenience in generating the bispecific antibody, in some embodiments, the bispecific antibody has a common light chain, and optionally a protein A-abrogating H95R modification in one of its CH3 domains. Thus, in some embodiments, the MS-ABP that is combined with the labeled target and assay cell is produced in a production cell transformed with a polynucleotide encoding the light chain, a polynucleotide encoding the target-specific heavy chain, and a polynucleotide encoding the destroyer-specific heavy chain. In some embodiments, the production cell supernatant containing the MS-ABP is combined with the labeled target and assay cell.

The production cell can be any cell. Commonly used production cells include e.g., insect cells, *E. coli, Pichia* and other yeast systems, avian cells, mammalian cells, primary cells, BSC cells, HeLa cells, HepG2 cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, CHO cells, CHO-K1 cells, NS-1 cells, MRC-5 cells, WI-38 cells, 3T3 cells, 293 cells, Per.C6 cells, chicken embryo cells and the like. In one embodiment, the production cell is a CHO cell or one or more of several specific CHO cell variants, such as the CHO-K1 cell line are optimized for large-scale protein production, or the EESYR® cell line (see U.S. Pat. No. 7,771,997 [issued Aug. 10, 2010]).

In some embodiments, the destroyer molecule is one that is known or discovered to rapidly turn over at the cell membrane. In some embodiments, the destroyer molecule is one that is known or discovered to rapidly clear a monospecific bivalent monoclonal antibody. In some embodiments, the destroyer molecule, when aggregated on the cell surface upon contact with inter alia (i) a multispecific antigen binding protein engaged with its cognate target (T), or (ii) a monospecific bivalent antigen binding protein (e.g., monospecific monoclonal antibody), is rapidly turned over or is rapidly cleared from the cell surface. In some embodiments, rapidly cleared or rapidly turned over includes clearance from the cell surface at a t½ (cell surface half-life) of <65 hours, <60 hours, <55 hours, <50 hours, <45 hours, <40 hours, <35 hours, <34 hours, <33 hours, <32 hours, <31 hours, <30 hours, <29 hours, <28 hours, <27 hours, <26 hours, <25 hours, <24 hours, <23 hours, <22 hours, <21 hours, <20 hours, <19 hours, <18 hours, <17 hours, <16 hours, <15 hours, <14 hours, <13 hours, <12 hours, <11 hours, <10 hours, <9 hours, <8 hours, <7 hours, <6 hours, <5 hours, <4 hours, <3 hours, <2 hours, <1 hours, or <30 minutes.

In some embodiments, the destroyer is known or discovered to traffics to or from the lysosome. A non-limiting list of useful destroyer molecules includes inter alia PCSK9, MHC-1, APLP2, LDLR, CD63, mannose-6-phosphate receptor (MPR), LIMP-2, sortilin, those internalization effectors listed herein (supra), and the like.

In some embodiments, the target molecule is a therapeutically relevant (therapeutic) target. A non-limiting list of useful target molecules includes inter alia IL-1, IL-1 receptor, IL-4, IL-4 receptor, VEGF, VEGF receptor, RSV, NGF, NGF receptor, programmed cell death protein-1 (PD1), programmed cell death protein ligand-1 (PD-L1), PD-L2, PDGF, PDGF receptor, angiopoietin-2 (Ang2), Ang2 receptor, myostatin (GDF8), GDF8 receptor, CD3, those targets listed herein (supra), and the like.

The target, if endocytosed by the assay cell mediated by the destroyer molecule, must be detectable. Therefore the target is modified with a detectable label. In some embodiments, that label is a fluorescent molecule. In some embodiments, the label is a pH-sensitive fluorophore, which changes its emission spectrum or intensity as the pH changes. One such useful pH-sensitive fluorophore is pHrodo® (red or green; Thermo Fisher Scientific, Waltham, Mass.), which is essentially non-fluorescent at neutral pH, and fluoresces with increasing intensity as the pH falls (e.g., as in early endosomes at pH ~6, late endosomes at pH ~5, and lysosomes at pH ~4.5-5). See for example Neaga et al., "Development and validation of a flow cytometric method to evaluate phagocytosis of pHrodo™ BioParticles® by granulocytes in multiple species," 390(1-2) J. Immunol. Methods. 9-17 (2013). Other pH sensitive dyes include cyanine dyes, such as e.g., CypHer™5E (GE Healthcare Life Sciences, See Beletskii, et al., "High-throughput phagocytosis assay utilizing a pH-sensitive fluorescent dye," 39 BioTechniques 894-897 (2005); and Shaner et al., "A guide to choosing fluorescent proteins," 2 Nature Methods 905-909 (2011). Other useful pH-sensitive dyes include LysoTracker Green DND-26 (ThermoFisher Cat #L7526); LysoSensor Green DND-189 (THermoFisher Cat #L7535) and others; LysoProbes I-IV (Yapici, N B, et al. 2015 Scientific Reports 5(8576):1-8).

In other embodiments, the label is a photostable fluorophore. One such useful photostable fluorophore is Alexa Fluor® 488. Other useful fluorophores include Alexa Fluor® 514, Alexa Fluor® 430, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 350, Alexa Fluor® 405, and the like, green fluorescent protein and its derivatives, rhodamine and rhodamine derivatives, Texas Red dyes, fluorescein and fluorescein derivatives, BODIPY® and other boron-dipyrromethenes and derivatives thereof, coumarin and coumarin derivatives, pyrenes, naphthalenes, and the like. See Molecular Probes™ Handbook, "A Guide to Fluorescent Probes and Labeling Technologies," 11$^{th}$ Edition (2010) available from Invitrogen at http://www.thermofisher.com/content/dam/LifeTech/global/technical-reference-library/MolecularProbesHandbook/chapter-pdfs/Ch-1-Fluorophores.pdf?icid=WE216841.

The label can be covalently linked to the target using commonly known crosslinking chemistry, such as inter alia N-hydroxysuccinimide (NHS) or sulfo-NHS esters, imidoesters, biotin-avidin systems, maleimides, haloacetyls (e.g., iodoacetyl), pyridyl disulfides, hydrazide reactions with carbonyls, carbodiimide reactions with carboxyls, photoreactive crosslinking with activated aryl nitrenes, and the like.

When a non-pH-sensitive label is used, both cell-surface and internalized label could potentially be detected. Here therefore, after the assay cell has been incubated for a sufficient time to allow internalization of the target, if such internalization were to occur, the cell is treated with a quencher. The quencher prevents, absorbs or otherwise masks light emitted from label sitting outside the cell, while having no effect on the internalized label. Therefore, in the presence of the quencher, only internalized label can be detected. In some embodiments, the quencher comprises an antibody or an antibody fragment, such as an Fab fragment. In some embodiments, the quencher is an anti-Alexa-fluor-488 antibody or an anti-Alexa-647 Fab.

In some embodiments, the internalized label is detected by any means known in the art. In some embodiments, the label is detected by flow cytometry. In other embodiments, the label is detected by high throughput microscopic imaging, such as e.g., the ImageXpress® System combined with high content image acquisition and analysis software (e.g., MetaXpress) (Molecular Devices, Sunnyvale, Calif.). See, e.g., Hua et al., "High-content positional biosensor screening assay for compounds to prevent or disrupt androgen receptor and transcriptional intermediary factor 2 protein-protein interactions," 12(7) Assay Drug Dev. Technol. 395-418 (2014).

The assay cell must express the destroyer protein. In some embodiments, the assay cell naturally expresses the destroyer molecule. In other embodiments, the assay cell is transfected with a polynucleotide encoding a destroyer molecule, such that the transfected assay cell ectopically expresses the destroyer. In some embodiments, the assay cell is a eukaryotic cell. In some embodiments, the assay cell is an animal or other metazoan cell. In some embodiments, the assay cell is a mammalian cell. In some embodiments, the assay cell is a rodent cell. In some embodiments, the assay cell is a mouse cell. In some embodiments, the assay cell is a primate cell. In some embodiments, the assay cell is a human cell. In some embodiments, the assay cell is a primary cell. In some embodiments, the assay cell is an immortalized cell. In some embodiments, the assay cell is a mouse cell that expresses a human destroyer protein. In some embodiments, the human cell is a HEK293 cell, a C1R-neo cell, or a HepG2 cell.

The MS-ABP may be made through an iterative process, whereby the destroyer-specific binding domain is selected first, and then the target-specific binding domain is selected to complete the pair. Alternatively, the target-specific binding domain is selected first, and then the destroyer-specific binding domain is selected to complete the pair. In one embodiment in which the MS-ABP is a bispecific antibody, the production cell is transformed with a polynucleotide encoding an antibody light chain, a polynucleotide encoding a target-specific heavy chain, and a polynucleotide encoding a destroyer-specific heavy chain. The production cell is incubated to allow it to express and secrete a bispecific antibody comprising a first arm that binds the target molecule and a second arm that binds the destroyer molecule. The production cell supernatant containing the bispecific antibody is collected and applied to the destroyer-expressing assay cell in the presence of the labeled target. The assay cell is incubated for a time sufficient to allow internalization of the target. The internalized label is then detected and the MS-ABP is selected.

In those embodiments in which the operator wishes to select an effective destroyer-specific binding domain (and wherein for example the MS-ABP is a bispecific antibody), the target-specific antibody heavy chain produced in the production cell is known to be an effective target-specific binding domain in an effective MS-ABP. In a specific embodiment, the target-specific heavy chain binds a myc epitope, and the labeled target contains a myc epitope. The target may be a myc-fusion protein. Here, the potential destroyer-specific binding domain is selected from among several potential effective destroyer-specific binding arms (the destroyer binding domain is the variable). A plurality of production cells contain individual different (e.g., as in a library) potential destroyer-specific binding domain-encoding polynucleotides. The potential MS-ABP is produced by the production cell and secreted into the production cell supernatant. The supernatants are then applied to the assay cells as described above, and any constructs demonstrating internalization of the labeled target are selected. The destroyer-specific heavy chain is concomitantly selected. In some embodiments, once the destroyer-specific heavy chain of the bispecific antibody is selected, it is sent back through the process, this time with the target-binding domain serving as the variable.

In those embodiments in which the operator wishes to select an effective target-specific binding domain (and wherein for example the MS-ABP is a bispecific antibody), the destroyer-specific antibody heavy chain produced in the production cell is known to be an effective destroyer-specific binding domain in an effective MS-ABP. In some embodiments, the destroyer-specific heavy chain binds an internalization effector protein herein described (supra). In some specific embodiments, the destroyer is inter alia PCSK9, APLP2, LDLR, CD63, mannose-6-phosphate receptor (MPR), LIMP-2, sortilin, or the like. In one embodiment, the known effective destroyer-specific binding domain is selected as described in the preceding paragraph (supra). In any of these embodiments, the potential target-specific binding domain is selected from among several potential effective target-specific binding arms (the target binding domain is the variable). A plurality of production cells contain individual different (e.g., as in a library) potential target-specific binding domain-encoding polynucleotides. The potential MS-ABP is produced by the production cell and secreted into the production cell supernatant. The supernatants are then applied to the assay cells as described above, and any constructs demonstrating internalization of the labeled target are selected. The target-specific heavy chain is concomitantly selected. In some embodiments, once the destroyer-specific heavy chain of the bispecific antibody is selected, it is sent back through the process, this time with the destroyer-binding domain serving as the variable.

As described above, in some embodiments, the target is a therapeutic target. In some specific embodiments, the target comprises IL-1, IL-1 receptor, IL-4, IL-4 receptor, VEGF, VEGF receptor, RSV, NGF, NGF receptor, programmed cell death protein-1 (PD1), programmed cell death protein ligand-1 (PD-L1), PD-L2, PDGF, PDGF receptor, angiopoietin-2 (Ang2), Ang2 receptor, myostatin (GDF8), GDF8 receptor, CD3, CD19, CD20, or the like.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

Example 1. Degradation of a Cell Surface Receptor

An exemplar multispecific antigen-binding molecule was created which is capable of binding (a) an internalizing effector molecule and (b) a cell surface receptor target molecule. In this Example, the internalizing effector protein is Kremen-2 (Krm2), and the cell surface receptor target molecule is an Fc receptor (FcγR1 [Fc-gamma-R1]).

Kremen molecules (Krm1 and Krm2) are cell-surface proteins known to mediate WNT signaling by directing the internalization and degradation of the WNT pathway signaling molecules LRP5 and LRP6. Internalization of LRP5/6 is accomplished via the soluble interacting protein DKK1. In particular, DKK1 links Kremen to LRP5/6 on the cell surface, and because of this linkage, the internalization of Kremen drives the internalization and degradation of LRP5 and LRP6. (See Li et al., PLoS One 5(6):e11014).

The inventors sought to exploit the Kremen-binding properties of DKK1 and the internalization properties of Kremen to induce the internalization of FcγR1. To facilitate Kremen-mediated internalization/degradation of FcγR1, a multispecific antigen-binding molecule was constructed consisting of DKK1 fused to a mouse Fc (DKK1-mFc, having the amino acid sequence of SEQ ID NO:1). As explained elsewhere herein, a multispecific antigen-binding molecule is defined as a molecule comprising a first antigen-binding domain (D1) which specifically binds a target molecule, and a second antigen-binding domain (D2) which specifically binds an internalizing effector protein. In this proof-of-concept Example, the "first antigen-binding domain" is the mFc component which specifically binds the target molecule FcγR1, and the "second antigen-binding domain" is the DKK1 component which specifically binds the internalizing effector protein Kremen.

An experiment was first conducted to determine whether DKK1-mFc can be endocytosed into cells in a Kremen-dependent manner. For this experiment, two cell lines were used: Cell-1, an HEK293 cell line engineered to express FcγR1 but not Kremen-2, and Cell-2, an HEK293 cell line engineered to express both FcγR1 and Kremen-2. A 1:10 dilution of DKK1-mFc conditioned medium was added to the respective cell lines and allowed to incubate at 37° C. for 90 minutes. After the 90 minute incubation, cells were stained with Alexa-488-labeled anti-mouse IgG antibody to detect the DKK1-mFc molecule. Using fluorescence microscopy, it was observed that virtually no DKK1-mFc was localized inside Cell-1 (lacking Kremen); however, substantial amounts of DKK1-mFc were detected within Cell-2 which expresses Kremen-2. Thus, these results show that the multispecific antigen-binding molecule DKK1-mFc can be internalized into cells in a Kremen-dependent manner.

Next, a time-course experiment was conducted to determine whether DKK1-mFc can induce FcγR1 degradation in a Kremen-dependent manner. A brief description of the experimental protocol is as follows: Cell-1 (expressing only FcγR1) and Cell-2 (expressing Kremen-2 and FcγR1) were treated with 2 mg/ml NHS-Sulfo-Biotin for 15 minutes on ice to label all cell surface expressed proteins. Cells were then washed and resuspended in 400 μl of medium and divided into four-100 μl aliquots which were treated with DKK1-mFc for varying amounts of time (0 min, 15 min, 30 min and 60 min) at 37° C. Following DKK1-mFc incubation, cells were pelleted and treated with protease inhibitors. Lysates of the cells from the different incubation time points were subjected to FcγR1 immunoprecipitation. For the FcγR1 immunoprecipitation, mouse anti-FcγR1 antibody was added to cell lysates and incubated for 1 hour at 4° C. Then Protein-G beads were added and the mixture was incubated for 1 hour at 4° C. The beads were then washed and the proteins eluted and subjected to SDS-PAGE. Proteins were transferred to membrane and probed with HRP-labeled streptavidin to reveal relative amounts of remaining surface-exposed FcγR1 protein in each sample. Results are shown in FIG. 2.

Figure 1:
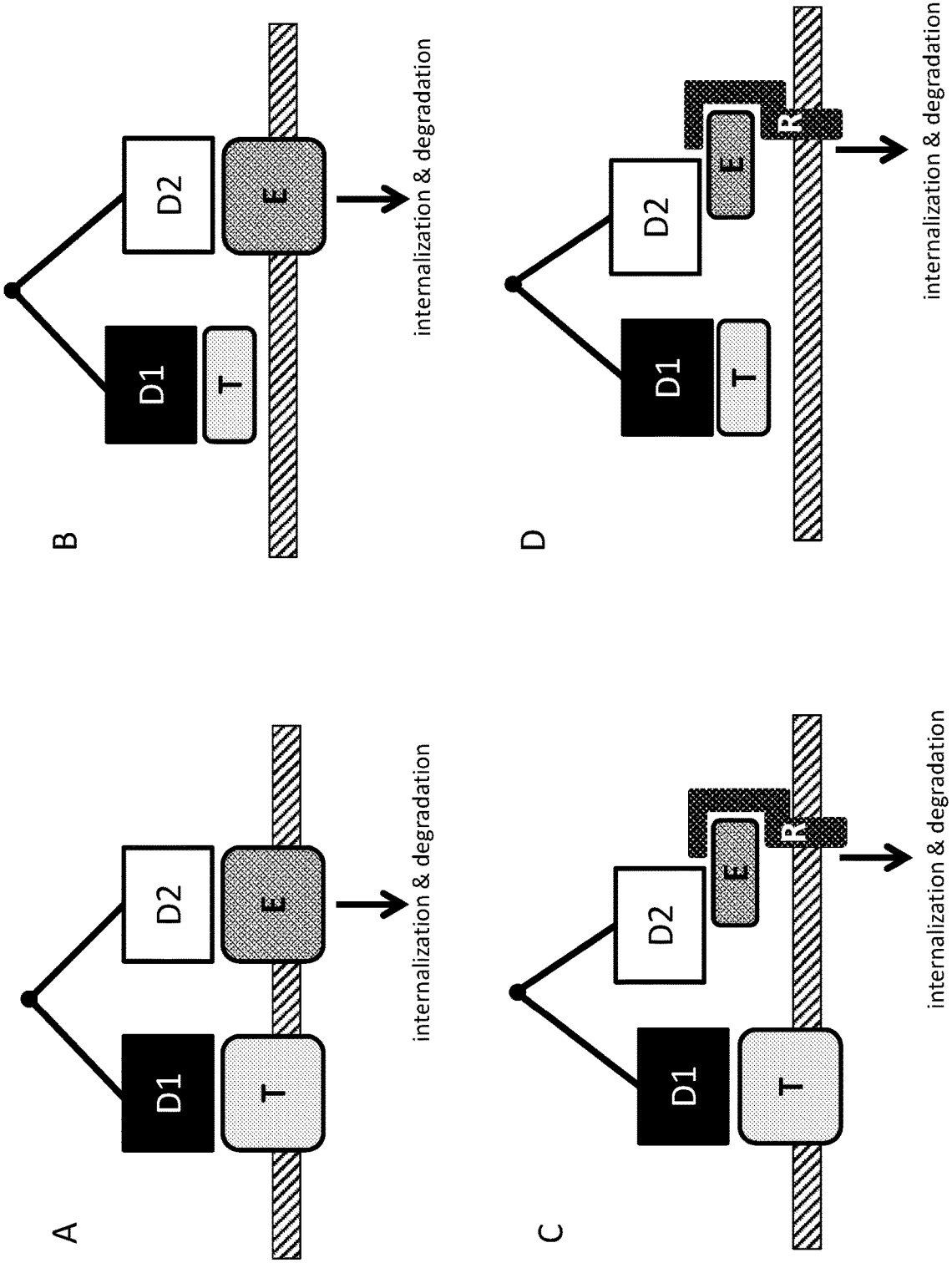
Figure 2:
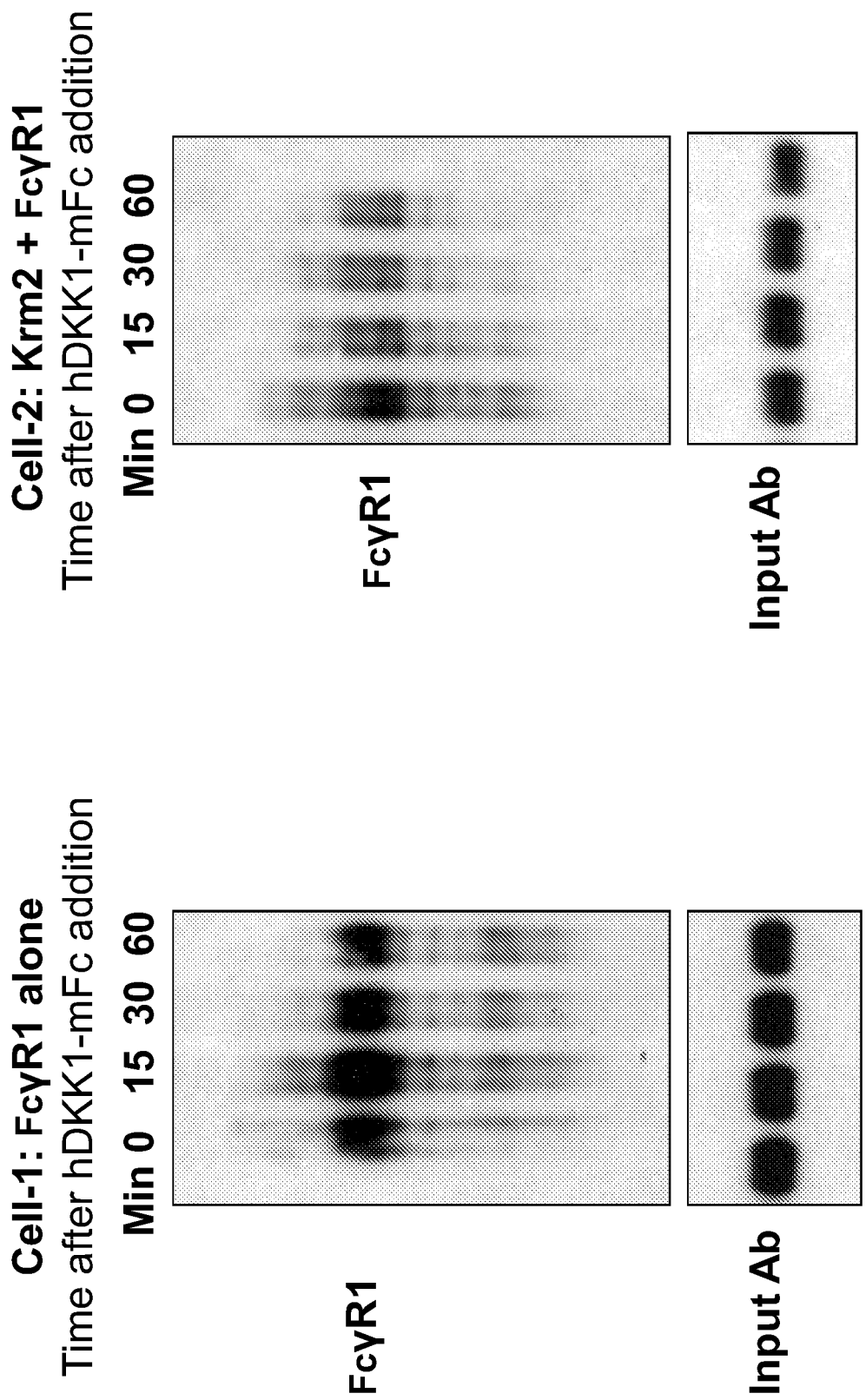
FIG. 2 shows the results of an immunoprecipitation experiment performed on two different cells (Cell-1 expressing FcγR1 alone, and Cell-2 expressing Krm2 and FcγR1) following incubation for different amounts of time (0, 15, 30 and 60 minutes) with a DKK1-mFc multispecific antigen-binding molecule.

As illustrated in FIG. 2, the amount of surface-exposed FcγR1 protein in Cell-1 samples (expressing FcγR1 but not Kremen-2) remained relatively constant regardless of the amount of time the cells were exposed to DKK1-mFc. By contrast, the amount of surface-exposed FcγR1 protein in Cell-2 samples (expressing both Kremen-2 and FcγR1) decreased substantially with increasing incubation times with DKK1-mFc. Thus, this experiment demonstrates that DKK1-mFc induces degradation of cell surface expressed FcγR1 in a Kremen-2-dependent manner.

Taken together, the foregoing results show that a multispecific antigen-binding molecule that simultaneously binds a cell surface target molecule (FcγR1) and an internalizing effector protein (Kremen-2), can induce degradation of the target molecule in an effector protein-dependent manner.

Example 2. IL-4R Attenuation with IL-4R×CD63 Multispecific Antigen-Binding Molecule An exemplar multispecific antigen-binding molecule was constructed which is capable of simultaneously binding a cell surface-expressed target molecule (i.e., IL-4R) and a cell surface-expressed internalizing effector protein (i.e., CD63). The purpose of these experiments was to determine whether IL-4R activity on a cell can be attenuated to a greater extent by physically linking IL-4R to an effector molecule that is internalized and targeted for degradation within the lysosome (in this case, CD63). In other words, this Example was designed to test whether the normal internalization and degradation of CD63 could be used to force the internalization and degradative rerouting of IL-4R within a cell.

First, a multispecific antigen-binding molecule was constructed that is able to bind both IL-4R and CD63. Specifically, a streptavidin-conjugated anti-IL-4R antibody and a biotinylated anti-CD63 antibody were combined in a 1:1 ratio to produce an anti-IL-4R:anti-CD63 conjugate (i.e., a multispecific antigen-binding molecule that specifically binds both IL-4R and CD63). The anti-IL-4R antibody used in this Example is a fully human mAb raised against the IL-4R extracellular domain. (The anti-IL-4R antibody comprised a heavy chain variable region having SEQ ID NO:3 and a light chain variable region having SEQ ID NO:4). The anti-CD63 antibody used in this Example is the mouse anti-human CD63 mAb clone MEM-259, obtained from Biolegend (San Diego, Calif.), catalog. No. 312002.

Two control constructs were also created: Control-1=streptavidin-conjugated anti-IL-4R antibody combined in a 1:1 ratio with biotinylated control mouse IgG1kappa antibody; and Control-2=streptavidin-conjugated anti-IL-4R antibody combined in a 1:1 ratio with non-biotinylated anti-CD63 antibody. The anti-IL-4R antibody used in the experimental and control constructs for this Example is an antibody that is known to specifically bind IL-4R and only partially block IL-4-mediated signaling.

The experimental cell line used in this Example is an HEK293 cell line containing a STAT6-luciferase reporter construct and additional STAT6 ("HEK293/STAT6-luc cells"). The cells used in this experiment express both IL-4R and CD63 on their surface. When treated with IL-4 in the absence of any inhibitors, this cell line produces a dose-dependent detectable chemiluminescence signal which reflects the extent of IL-4-mediated signaling.

Anti-IL-4R/anti-CD63 multispecific molecule, or the control constructs, were added to the HEK293/STAT6-luc cells so that the final concentration of anti-IL-4R antibody in the media was 12.5 nM. Reporter signal was measured at increasing concentrations of IL-4 in the presence and absence of the experimental and control constructs (FIG. 3). As shown in FIG. 3, The anti-IL-4R/anti-CD63 multispecific molecule ("ab conjugate") inhibited IL-4-mediated signaling to a significantly greater extent than either control construct.

To confirm that the effect observed in FIG. 3 was dependent on CD63, the same experiment described above was carried out, except that CD63 expression was significantly reduced in the reporter cell line using an siRNA directed against CD63. With CD63 expression significantly reduced, the enhanced inhibitory activity of the anti-IL-4R/anti-CD63 multispecific molecule was no longer observed (FIG. 4). This result suggests that the ability of the anti-IL-4R/anti-CD63 multispecific molecule to attenuate IL-4-mediated signaling is due to the simultaneous binding of the multi-specific molecule to IL-4R and CD63 and the consequent internalization and degradation of the entire antibody-IL-4R-CD63 complex.

Similar experiments were next carried out in which the anti-IL-4R/anti-CD63 multispecific molecule, or the control constructs, were allowed to incubate with the HEK293/STAT6-luc reporter cell line for various amounts of time prior to the addition of IL-4. In a first set of such experiments, the molecules were allowed to incubate with the reporter cell line for 0 hours (i.e., added concurrently with IL-4), 2 hours, or overnight prior to the addition of 50 ρM IL-4. Luciferase activity was measured six hours after the addition of IL-4. Results are shown in FIG. 5, top panel ("untransfected"). In a further set of experiments, a similar protocol was carried out, except that the experimental or control molecules were allowed to incubate with the reporter cell line for 15 minutes, 30 minutes, 1 hour or 2 hours prior to the addition of 50 ρM IL-4. Results are shown in FIG. 6.

The results summarized in FIGS. 5 and 6 show that the anti-IL-4R/anti-CD63 multispecific molecule is able to inhibit IL-4-mediated signaling, and that this inhibitory effect is enhanced with longer incubation times. As with the initial set of experiments, it was confirmed using CD63 siRNA that the inhibitory effect of the anti-IL-4R/anti-CD63 multispecific molecule was dependent on CD63 expression (FIG. 5 bottom panel ["CD63 siRNA"]).

In summary, this Example provides further proof-of-concept for the inhibition of a target molecule activity through the use of a multispecific antigen-binding molecule that is capable of simultaneously binding both the target molecule (in this case IL-4R) and an internalizing effector protein (in this case CD63) to thereby cause the internalization and degradative rerouting of the target molecule within a cell. Stated differently, the simultaneous binding of IL-4R and CD63 by the exemplary multispecific antigen-binding molecule attenuated the activity of IL-4R to a substantially greater extent (i.e., >10%) than the binding of IL-4R by the control constructs alone.

Example 3. Anti-IL-4R×Anti-CD63 Bispecific Antibody Attenuates IL-4R in a CD63-Dependent Manner The experiments of Example 2, herein, show that an anti-IL-4R/anti-CD63 multispecific molecule inhibits IL-4-mediated signaling in a CD63-dependent manner. In those experiments, the multispecific antigen-binding molecule consisted of two separate monoclonal antibodies (anti-IL-4R and anti-CD63) that were connected via a biotin-streptavidin linkage. To confirm that the results observed with that proof-of-concept multispecific antigen-binding molecule are generalizable to other multispecific antigen-binding molecule formats, a true bispecific antibody was constructed.

Standard bispecific antibody technology was used to construct a bispecific antibody consisting of a first arm specific for IL-4R and a second arm specific for CD63. The IL-4R-specific arm contained an anti-IL-4R heavy chain paired with a CD63-specific light chain. The CD63-specific light chain was paired with the IL-4R specific heavy chain solely for purposes of convenience of construction; nevertheless, the pairing of the anti-IL-4R heavy chain with the anti-CD63 light chain retained full specificity for IL-4R and did not exhibit binding to CD63. The CD63-specific arm contained an anti-CD63 heavy chain paired with an anti-CD63 light chain (the same light chain as used in the IL-4R arm). The anti-IL-4R heavy chain (comprising SEQ ID NO:3) was derived from the full anti-IL-4R antibody as used in Example 2; However, the anti-CD63 heavy and light chains were derived from the anti-CD63 antibody designated H5C6, obtained from the DevelopMental Studies Hybridoma Bank (University of Iowa Department of Biology, Iowa City, Iowa). As with the full anti-IL-4R antibody used in Example 2, the anti-IL-4R component of the bispecific antibody used in this Example exhibited only moderate IL-4R blocking activity on its own.

An IL-4 luciferase assay was carried out to assess the blocking activity of the anti-IL-4R x anti-CD63 bispecific antibody. Briefly, serial dilutions of anti-IL-4R×anti-CD63 bispecific antibody or control molecules were added to HEK293/STAT6-luc reporter cells (see Example 2). Under normal conditions, these cells produce a detectable luciferase signal when treated with IL-4. For this experiment, 10 pM IL-4 was then added to the cells, and luciferase activity was quantified for each dilution of antibody used. The controls used in this assay were: (a) mock bispecific antibody that binds IL-4R with one arm and has a non-functional anti-CD63 arm (i.e., containing one anti-IL-4R heavy chain and one anti-CD63 heavy chain, both paired with the anti-IL-4R light chain); (b) anti-IL-4R monospecific antibody; and (c) buffer (PBS) only (without antibody). Results are shown in FIG. 7. As shown in FIG. 7, for the control samples used, luciferase activity remained relatively high even at the highest antibody concentrations, whereas for the bispecific antibody, luciferase activity declined significantly as antibody concentration increased. These results confirm that simultaneous binding of IL-4R and CD63 by a bispecific antibody causes substantial inhibition of IL-4R activity.

Example 4. Internalization of SOST Using a SOST×CD63 MS-ABP

The ability of multispecific antigen-binding molecules to promote the internalization of the soluble target molecule SOST (sclerostin) was assessed. For these experiments, the target molecule was a fusion protein consisting of a human SOST protein tagged with a pHrodo™ moiety (Life Technologies, Carlsbad, Calif.) and a myc tag. The pHrodo™ moiety is a pH-sensitive dye that is virtually non-fluorescent at neutral pH and brightly fluorescent in an acidic environment such as the endosome. The fluorescent signal, therefore, can be used as an indicator of cellular internalization of the SOST fusion protein. The multispecific antigen-binding molecules for these experiments were bispecific antibodies with binding specificity for both CD63 (an internalizing effector protein) and the SOST fusion protein (a soluble target molecule), as described in more detail below.

The experiments were conducted as follows: Briefly, HEK293 cells were plated at 10,000 cells/well in poly-D-lysine coated 96 well plates (Greiner Bio-One, Monroe, N.C.). After allowing the cells to settle overnight, the media was replaced with media containing antibody (5 μg/mL, as described below), pHrodo™-myc-tagged-SOST (5 μg/mL), heparin (10 μg/mL), and Hoechst 33342. The cells were then incubated for either 3 hours on ice or 3 hours at 37° C. All cells were washed twice prior to imaging in PBS, and the number of fluorescent spots per cell, as well as the corresponding fluorescence intensity, was counted to establish the extent of pHrodo-myc-tagged-SOST cellular internalization in the presence of the various antibody constructs.

The antibodies used in this Example were as follows: (1) anti-CD63 monospecific antibody (clone H5C6, DevelopMental Studies Hybridoma Bank, University of Iowa Department of Biology, Iowa City, Iowa); (2) anti-myc antibody (clone 9E10, Schiweck et al., 1997, FEBS Lett. 414(1):33-38); (3) anti-SOST antibody (an antibody having the heavy and light chain variable regions of the antibody designated "Ab-B" in U.S. Pat. No. 7,592,429); (4) anti-CD63×anti-myc bispecific antibody (i.e., a multispecific antigen-binding molecule comprising an anti-CD63 arm derived from the antibody H5C6 and an anti-myc arm derived from 9E10); (5) anti-CD63×anti-SOST bispecific antibody #1 (i.e., a multispecific antigen-binding molecule comprising an anti-CD63 arm derived from the antibody H5C6 and an anti-SOST arm derived from "Ab-B"); and (6) anti-CD63×anti-SOST bispecific antibody #2 (i.e., a multispecific antigen-binding molecule comprising an anti-CD63 arm derived from the antibody H5C6 and an anti-SOST arm derived from the antibody designated "Ab-20" in U.S. Pat. No. 7,592,429). The bispecific antibodies used in these experiments were assembled using the so-called "knobs-into-holes" methodology (see, e.g., Ridgway et al., 1996, Protein Eng. 9(7):617-621).

Results of the internalization experiments are shown in FIG. 8. FIG. 8 shows the number of spots (labeled vesicles) per cell, under the various treatment conditions tested. Taken together, the results of these experiments demonstrate that the bispecific constructs, which simultaneously bind CD63 and SOST (either directly or via the myc tag), caused the greatest amount of SOST internalization as reflected by the fluorescence intensity and number of fluorescent spots per cell over time at 37° C. Thus, the multispecific antigen-binding molecules used in this Example are able to effectively direct the internalization of a soluble target molecule.

Example 5. Changes in Bone Mineral Density in Mice Treated with SOST×CD63 MS-ABP An anti-CD63×anti-SOST multispecific antigen-binding molecule, as described in Example 4, is next tested for its ability to increase bone mineral density in mice. Five groups of mice (about 6 mice per group) are used in these experiments. The treatment groups are as follows: (I) untreated negative control mice; (II) mice treated with a blocking anti-SOST monospecific antibody that is known to increase bone mineral density on its own (positive control); (III) mice treated with a bispecific antibody that specifically binds CD63 and SOST but does not inhibit SOST activity on its own or only slightly inhibits SOST activity on its own; (IV) mice treated with an anti-CD63 parental antibody (i.e., a monospecific antibody containing the same anti-CD63 antigen-binding domain as in the bispecific antibody); and (V) mice treated with an anti-SOST parental antibody (i.e., a monospecific antibody containing the same anti-SOST antigen-binding domain as in the bispecific antibody). The amount of antibody administered to the mice in each group is about 10 to 25 mg/kg.

It is expected that mice in group III (treated with an anti-SOST×anti-CD63 bispecific antibody) will exhibit an increase in bone mineral density that is at least comparable to that which is observed in the mice of group II (treated with a known blocking anti-SOST antibody), even though the anti-SOST component of the bispecific antibody does not inhibit SOST activity on its own (as confirmed by the mice in Group V which are expected to not exhibit an increase in bone mineral density). The increase in bone mineral density that is expected in the mice of group III is believed to be driven by CD63-mediated internalization of SOST, as observed in the cellular experiments of Example 4, above.

Example 6. Internalization of Lipopolysaccharide (LPS) by LPS×CD63 MS-ABP

This Example illustrates the use of a multispecific antigen-binding molecule of the invention to direct the internalization of a non-protein target molecule, namely lipopolysaccharide (LPS). LPS is a component of the outer membrane of Gram-negative bacteria and is known to contribute to septic shock. Anti-LPS antibodies have been investigated as possible treatment agents for sepsis. The experiments of the present Example were designed to assess the ability of a multispecific antigen-binding molecule to promote the internalization of LPS.

The multispecific antigen-binding molecule used in this Example was a bispecific antibody with one arm directed to LPS (target) and the other arm directed to CD63 (internalizing effector protein). The anti-LPS arm was derived from the antibody known as WN1 222-5. (DiPadova et al., 1993, *Infection and Immunity* 61(9):3863-3872; Muller-Loennies et al., 2003, *J. Biol. Chem.* 278(28):25618-25627; Gomery et al., 2012, *Proc. Natl. Acad. Sci USA* 109(51):20877-20882; U.S. Pat. No. 5,858,728). The anti-CD63 arm was derived from the H5C6 antibody (see Example 4). The anti-LPS×anti-CD63 bispecific antibody (i.e., multispecific antigen-binding molecule) was assembled using the so-called "knobs-into-holes" methodology (see, e.g., Ridgway et al., 1996, Protein Eng. 9(7):617-621).

Two LPS species were used in these experiments: *E. coli* LPS and *Salmonella minnesota* LPS. Both versions were obtained as fluorescent-labeled molecules (ALEXA-FLUOR®-488-labeled LPS, Life Technologies, Carlsbad, Calif.).

Experiments were conducted as follows: HEK293 cells were plated in 96-well PDL-coated imaging plates. After overnight rest, media was replaced with fresh medium. Fluorescently labeled LPS (either *E. coli*- or *S. minnesota*- derived) was added in regular medium. Next, the anti-LPS× anti-CD63 bispecific antibody, or control half-antibodies paired with dummy Fc, were added to the samples. Following various incubation times at 37° C. (1 hour and 3 hours) or on ice (3 hours), cells from the LPS-treated samples were processed as follows: washed—quenched with anti-ALEXA-FLUORO-488 antibody—washed & fixed. The anti-ALEXA-FLUOR®-488 antibody quenches fluorescence from non-internalized (i.e., surface bound) fluorophore. Thus, any fluorescence observed in the quenching antibody-treated samples is due to internalized LPS. The level of fluorescence from each sample at the various time points was measured.

FIG. 9 expresses the results of these experiments in terms of the number of labeled vesicles per cell. As shown in FIG. 9, only cells treated with the anti-CD63×anti-LPS bispecific antibody demonstrated significant numbers of labeled vesicles that increased over time. Cells treated with labeled LPS and the control antibodies did not exhibit appreciable numbers of fluorescent vesicles, indicating that LPS was not internalized under those treatment conditions.

This Example therefore demonstrates that an anti-LPS× anti-CD63 bispecific antibody causes internalization of LPS into cells in a manner that requires simultaneous binding of LPS and CD63. Accordingly, these results support the use of multispecific antigen-binding molecules of the invention to promote cellular internalization of target molecules such as LPS for the treatment of diseases and disorders such as sepsis.

Example 7. Selection of MS-ABP Binding Domains

In this example, the exemplar destroyer molecule was the major histocompatibility complex I, B isoform (a.k.a. HLA-B). HLA-B was selected in part as the destroyer since tight binding monoclonal antibodies were rapidly cleared by cells. This is a hallmark of a "destroyer" molecule. As an exemplar soluble target molecule, the allergen FelD1 was selected as the target molecule. FelD1 is a tetrameric glycoprotein comprising two disulfide linked heterodimers. Two forms of soluble FelD1 were constructed and tested, a FelD1-myc-myc-his fusion protein (FelD1-mmh) and a FelD1-Fc fusion protein.

In one set of experiments, FelD1-mmh was labeled with Alexa Fluor 488 to aid in tracking the internalization of the target. A bispecific antibody comprising an HLA-B-specific arm (binds destroyer) and a FelD1-specific arm (binds target) (α-HLAB27•α-FelD1) was used as the multispecific antigen-binding protein. FelD1-mmh was labeled with Alexa Fluor®488. C1Rneo B-lymphoblastoid cells expressing HLA-B were used as the assay cell and incubated with 10 μg/ml FelD1-mmh-Alexa Fluor® 488, and 10 μg/ml α-HLAB27•α-FelD1. The cells were incubated overnight to allow time for internalization of the labeled FelD1 target protein. The cells were then incubated with a quencher, i.e., anti-Alexa488 antibody (Alexa-Fluor-488-Antibody-Polyclonal/A-11094, Thermo Fisher Scientific, Waltham, Mass.)), which quenches the fluorescence of Alexa488. The anti-Alexa488 antibody will not quench labeled target that has been internalized, therefore internalized target can be distinguished from target that is associated with the surface of the cell. Here, fluorescence was quantified by flow cytometry.

FIG. 10 depicts the mean fluorescence (arbitrary units quantified by FACS) of surface-bound target and internalized target, for both MHC1 negative cells, which serve as controls, and MHC1 positive cells. The bispecific antibody used was α-HLAB27•α-FelD1. The parent α-HLAB27 bivalent antibody and non-specific IgG isotype were used as controls. For those cells expressing the MHC1 (destroyer), the cells contacted with α-HLAB27•α-FelD1 showed an approximately four-fold increase in internalized target molecule relative to surface-associate target molecule. Essentially no effect was detected for the controls. The results are depicted in FIG. 10 and in Table 1 below.

TABLE 1

Mean Fluorescence Units (FelD1-mmh-Alexa288)

| Antibody | C1R neo B-Lymphoblastoid Cells | | | |
|---|---|---|---|---|
| | MHC minus cells | | MHC plus cells | |
| | Surface | Internalized | Surface | Internalized |
| α-HLAB27•α-FelD1 | <500 | <500 | ~825 | ~3,350 |
| Parental α-HLAB27 | <500 | <500 | <500 | <500 |
| Isotype control | <500 | <500 | <500 | <500 |

The α-HLAB27•α-FelD1 MS-ABP selected by the assay was demonstrated to be effective in vivo. Bispecific antibody α-HLAB27•α-FelD1 and controls (PBS, anti-FelD1 bivalent monospecific, and anti-HLAB27 bivalent monospecific) were administered to mice expressing a human HLA-B allele by subcutaneous injection (10 mg/kg). The following day, 1.6 mg/kg of FelD1-Fc DNA was administered by tail vein injection. (A 3:1 antibody:target ratio was used.) Serum samples were obtained from tail bleeds taken at 15 minutes, 6 hours, 1 day, 2 days, 3 days, 4 days, 6 days, and 8 days. FelD1 levels were detected and quantified by Western blotting using anti-FelD1 antibodies. The α-HLAB27•α-FelD1 bispecific treatment demonstrated fast FelD1 clearance with a t½ of <30 hours, similar to the clearance rate of anti-HLAB27 in the absence of FelD1 (i.e., t½ of 33 hours) and more than twice the clearance rate of α-HLAB27•α-FelD1 in the absence of FelD1 (i.e., t½ of 65 hours). The administration of anti-FelD1 did not affect MHC1-mediated clearance, but some moderate clearance was observed, which is attributed to Fc receptors.

Example 8. Step-Wise Selection of Binding Domains

A panel of monospecific and bispecific antibodies was tested to evaluate internalization. Here, CD63 antibodies and anti-CD63×anti-myc bispecific antibodies were evaluated for their ability to be internalized by HEK293 cells that express CD63, in the absence of any target. Any cell line that expresses CD63 could be used for this assay. Briefly, HEK293 cells were incubated with 1 µg/ml antibody and 1 µg/ml anti-human IgG secondary Fab Alexa® 647 for 3 hours followed by imaging on an ImageXpress® high content imager (Molecular Devices, Sunnyvale, Calif.).

Interestingly, the effective internalization of a bivalent antibody did not correlate with how well a bispecific antibody incorporating that antibody as one arm would perform in the internalization assay. This suggests the importance of having two or more internalization effector-specific binding domains available for binding, to increase avidity and/or to promote clustering of receptors at the cell surface. For example, the bivalent monospecific anti-CD63 Ab3 internalizes well, as does the bispecific anti-CD63 Ab3×anti-Myc; on the other hand anti-CD63 Ab6 internalizes well but the bispecific anti-CD63 Ab6×anti-Myc is not internalized at all (FIG. 11). Of six CD63-specific antibodies, all of the bivalent monospecific forms were internalized, but only 50% internalized when the internalizing effector antibody arm was paired with a second arm (as one half of a bispecific), while the other 50% failed to internalize. This assay allows one to select an effective destroyer binding arm, suitable for inclusion with a target binding arm in making an MS-ABP that destroys a target molecule.

The bispecific anti-CD63×anti-Myc antibodies that were internalized well were then evaluated for internalization of a specific target, in this case hemojuvelin (HJV). HJV is a co-receptor for bone morphogenic protein 6 (BMP6). Blocking HJV inhibits BMP6 signaling and decreases hepcidin levels, which in turn inhibits the iron transporter ferroportin. Ultimately, blocking HJV increases serum iron, which is a convenient in vivo assay for an effective MS-ABP pair.

The Anti-CD63 arms that worked well in the bispecific form (supra) were then paired with anti-HJV (anti-target) antibody arms to make several anti-CD63×anti-HJV antibodies. Anti-CD63×anti-Myc is used as a positive control in the assay. HEK293 cells were incubated with 10 µg/ml antibody and 1 µg/ml pHrodo®-labeled HJV-myc-myc-his for either 1 or 3 hours, followed by imaging on the ImageXpress® high content imager and quantification using MetaXpress software (Molecular Devices, Sunnyvale, Calif.). Although both anti-HJV1×anti-CD63 and anti-HJV2×anti-CD63 internalize HJV, significant differences in their internalization-promoting effectiveness were revealed by this assay. FIG. 12 depicts the differences between internalization between the HJV1 arm and the HJV2 arm, with HJV2 showing more than twice the late endosomal/lysosomal fluorescence than HJV1 (FIG. 12). While the parental bivalent antibodies were tested (anti-HJV 1, anti-HJV2, anti-Myc, and anti-CD63), none showed signal indicative of target internalization.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

What is claimed is:

1. An iterative method of making a therapeutic multispecific antigen-binding protein (MS-ABP), the method comprising the steps of:
 (a) incubating one of a plurality of assay cells that express a destroyer molecule with
  (i) one of a plurality of different MS-ABPs such that each different MS-ABP may be correlated with only one of the plurality of assay cells wherein each of the plurality of different MS-ABPs comprises a destroyer-specific binding domain and a tag-specific binding domain, and
  (ii) a tag, wherein the tag-specific binding domain binds the tag;
 (b) detecting intracellular internalization of the tag by at least one of the plurality of incubated assay cells; and
 (c) physically linking
  (i) a destroyer-specific binding domain from one of the plurality of different MS-ABPs that correlates to the at least one of the plurality of incubated assay cells having the tag detected intracellularly, and
  (ii) a therapeutic target-specific binding domain to make the therapeutic MS-ABP, which is capable of physically linking a therapeutic target molecule to the destroyer molecule and thereby facilitate the degradative rerouting of the therapeutic target molecule intracellularly,
 wherein the therapeutic MS-ABP is capable of physically linking the therapeutic target molecule to the destroyer molecule and thereby facilitating the degradative rerouting of the therapeutic target molecule intracellularly;
 wherein the tag-specific binding domain comprises a myc-specific binding arm, and the tag comprises a myc epitope; and
 wherein the tag is linked to at least one label, and the at least one label is a fluorescent molecule.

2. The method of claim 1, further comprising selecting the therapeutic target-specific binding domain by:
 (a) combining
  (i) a destroyer-specific binding protein of the one of the plurality of different MS-ABPs that is correlated with the at least one of the plurality of assay cells in which intracellular internalization of the tag is detected, and
  (ii) one of a plurality of target-specific binding arms;
 (b) incubating one of a plurality of assay cells that express the destroyer molecule with
  (i) the destroyer-specific binding protein combined with the one of a plurality of target-specific binding arms, and
  (ii) the target molecule;
 (c) detecting the target molecule within the cell; and
 (d) selecting, as the therapeutic target-specific binding domain, the one of the plurality of target specific-binding domains if the target molecule is detected within the cell.

3. The method of claim 1, wherein the therapeutic MS-ABP is a bispecific antibody.

4. The method of claim 3, wherein the bispecific antibody comprises a common light chain.

5. The method of claim 3, wherein the bispecific antibody comprises a first arm that comprises the therapeutic target-specific binding domain and a second arm that comprises the destroyer-specific binding domain.

6. The method of claim 5, wherein the first arm is an scFv molecule, the second arm is an scFv molecule, or both arms are scFv molecules.

7. The method of claim 1, wherein the destroyer molecule is a molecule that is rapidly turned over, rapidly clears a monospecific bivalent monoclonal antibody, traffics to or from the lysosome, or any combination thereof.

8. The method of claim 7, wherein the MS-ABP molecule is cleared from the surface of the cell with a t½ of <65 hours, <33 hours, or <30 hours.

9. The method of claim 8, wherein the destroyer molecule is selected from the group consisting of transferrin receptor, ASGR1, ASGR2, CD36, PCSK9, MHC-1, APLP2, LDLR, CD63, mannose-6-phosphate receptor (MPR), LIMP-2, and sortilin.

10. The method of claim 1, wherein the therapeutic target molecule is selected from the group consisting of IL-1, IL-1 receptor, IL-4, IL-4 receptor, VEGF, VEGF receptor, RSV, NGF, NGF receptor, programmed cell death protein-1 (PD1), programmed cell death protein ligand-1 (PD-L1), PD-L2, PDGF, PDGF receptor, angiopoietin-2 (Ang2), Ang2 receptor, myostatin (GDF8), GDF8 receptor, CD3, and CD20.

11. The method of claim 1, wherein the fluorescent molecule is selected from the group consisting of pHrodo, LysoTracker Green DND-26, LysoSensor Green DND-189, and LysoProbes I-IV.

12. The method of claim 1, further comprising the step of contacting the cell after step 1(a) and before step 1(b) with a molecule that quenches the label at the cell surface.

13. The method of claim 12, wherein the molecule that quenches the label comprises a label-binding antibody or fragment thereof.

14. The method of claim 13, wherein the molecule that quenches the label is an anti-Alexa-fluor-488 antibody or an anti-Alexa-647 Fab.

15. The method of claim 1, wherein the tag is detected via flow cytometry, fluorescence imaging, or confocal microscopy.

16. The method of claim 1, wherein the assay cells naturally or ectopically express the destroyer molecule on their surfaces.

17. The method of claim 1, wherein the assay cells are mammalian.

18. The method of claim 1, wherein the assay cells express a human destroyer molecule.

19. The method of claim 17, wherein the assay cells are human.

20. The method of claim 19, wherein the assay cells are ex vivo.

21. The method of claim 20, wherein the assay cells are selected from the group consisting of primary cells, HEK293 cells, C1R-neo cells, and HepG2 cells.

22. The method of claim 1, further comprising the steps of:
(a) transforming a production cell with a polynucleotide encoding an antibody light chain, a polynucleotide encoding a tag-specific binding protein heavy chain, and a polynucleotide encoding a destroyer-specific binding protein heavy chain;
(b) allowing the production cell to express and secrete a bispecific antibody comprising (i) the different destroyer-specific binding domain that binds the destroyer molecule combined with (ii) the tag-specific binding domain that binds the tag; and
(c) collecting the production cell supernatant containing the bispecific antibody for use in step 1(a) as one of the plurality of different MS-ABPs.

23. The method of claim 22, wherein the tag-specific binding protein heavy chain is derived from a bivalent tag-specific monoclonal antibody.

24. The method of claim 23, wherein the destroyer molecule is selected from the group consisting of transferrin receptor, ASGR1, ASGR2, CD36, PCSK9, MHC-1, APLP2, LDLR, CD63, mannose-6-phosphate receptor (MPR), LIMP-2, and sortilin.

25. The method of claim 24, wherein the target molecule is selected from the group consisting of IL-1, IL-1 receptor, IL-4, IL-4 receptor, VEGF, VEGF receptor, RSV, NGF, NGF receptor, programmed cell death protein-1 (PD1), programmed cell death protein ligand-1 (PD-L1), PD-L2, PDGF, PDGF receptor, angiopoietin-2 (Ang2), Ang2 receptor, myostatin (GDF8), GDF8 receptor, CD3, and CD20.

26. The method of claim 2, wherein the target molecule is linked to a label.

* * * * *